United States Patent [19]

Faull et al.

[11] Patent Number: 5,219,874

[45] Date of Patent: Jun. 15, 1993

[54] HETEROCYCLIC ACIDS

[75] Inventors: Alan W. Faull, Macclesfield, England; Keith Russell, Newark, N.J.; William J. Watkins, Macclesfield, England

[73] Assignee: Imperial Chemical Industries PLC, London, England

[21] Appl. No.: 763,304

[22] Filed: Sep. 20, 1991

[51] Int. Cl.$^5$ ............... C07C 417/04; C07C 405/04; A61K 31/415; A61K 31/425

[52] U.S. Cl. ............................ 514/365; 514/397; 548/204; 548/311.1

[58] Field of Search ............. 548/204, 336, 311.1; 514/365, 397

[56] References Cited

U.S. PATENT DOCUMENTS

| | | | |
|---|---|---|---|
| 4,567,197 | 1/1986 | Brewster et al. | 514/452 |
| 4,668,698 | 5/1987 | Brewster | 514/452 |
| 4,704,399 | 11/1987 | Main | 514/452 |
| 4,723,037 | 2/1988 | Harris | 514/452 |
| 4,735,963 | 4/1988 | Matassa et al. | 514/452 |
| 4,736,057 | 4/1988 | Guildford | 514/452 |
| 4,772,625 | 9/1988 | Brewster et al. | 514/452 |
| 4,775,684 | 10/1988 | Smithers | 514/452 |
| 4,775,685 | 10/1988 | Brewster et al. | 514/452 |
| 4,806,563 | 2/1989 | Smithers | 514/452 |
| 4,822,815 | 4/1989 | Brown et al. | 514/452 |
| 4,824,858 | 4/1989 | Brown et al. | 514/452 |
| 4,831,046 | 5/1989 | Brown et al. | 514/452 |
| 4,845,120 | 7/1989 | Brown et al. | 514/452 |
| 4,902,712 | 2/1990 | Smithers | 514/452 |
| 4,908,380 | 3/1990 | Brewster et al. | 514/452 |
| 4,921,866 | 5/1990 | Brewster et al. | 514/452 |
| 4,925,869 | 5/1990 | Smithers | 514/452 |
| 5,051,530 | 9/1991 | Chang et al. | 560/184 |
| 5,053,415 | 10/1991 | Brewster et al. | 514/452 |
| 5,053,415 | 10/1991 | Brewster | 514/336 |
| 5,072,008 | 12/1991 | Harris | 514/452 |

FOREIGN PATENT DOCUMENTS 0329360 8/1989 European Pat. Off. .
0346511 12/1989 European Pat. Off. .

OTHER PUBLICATIONS

Sinkula, A. A. "Prodrug Approach in Drug Design" In *Ann. Rep. Med. Chem.* (1975), 10, 306–316.

Stella, V. "Pro-drugs: An Overview and Definition" and Sinkula, A. A., Application of the Pro-drug Approach to Antibiotics In *Pro–drugs as Novel Drug Delivery Systems*; Higuchi, T. and Stella, V. Eds.; ACS Symposium Series 14, American Chemical Society: Washington, DC, 1975; pp. 1–15, 44–45, 116–153.

Bundgaard, H. "Design of prodrugs: Bioreversible derivatives for various functional groups and chemical entities" In *Design of Prodrugs*; Bundgaard, H., Ed.; Elsevier Science Publishers: Amsterdam, 1985; pp. 1–10.

Bundgaard, H., "Design of Bioreversible Drug Derivatives and the Utility of the Double Prodrug Concept" In *Bioreversible Carriers in Drug Design*; Roche, E. B., Ed.; Pergamon Press: New York, 1987; pp. 13–21.

Kaneo, M. et al., Thromboxane A$_2$ Synthesis Inhibitors. I. Synthesis and Activities of Various N-Heteroaromatic Derivatives, *Chem. Pharm. Bull.* (1988), 36, 2968–2976.

*Primary Examiner*—Robert Gerstl
*Attorney, Agent, or Firm*—Thomas E. Jackson

[57] ABSTRACT

The invention concerns novel 1,3-dioxane alkenoic acid derivatives of the formula I

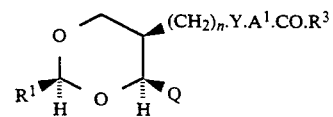

wherein:
 n is the integer 1 or 2;
 Y is methyleneoxy, vinylene or ethylene;
 $A^1$ is (1–6C)alkylene;
 $R^1$ is a group of the formula $R^2.A^2$—, in which:
  $R^2$ is phenyl unsubstituted or bearing up to three substituents which are independently selected from (1–6C)alkyl, (1–6C)alkoxy, (2–6C)alkanoyl, (1-6C)alkylthio, (1-6C)alkylsulphonyl, halogeno, trifluoromethyl, nitro and cyano;

$A^2$ is a direct bond to $R^2$ or a group of the formula —W—C($R^4$)($R^5$)— wherein W is oxygen, methylene or a direct bond to $R^2$, and $R^4$ and $R^5$ are independently (1-4C)alkyl;

Q is a heterocyclyl group selected from thiazol-5-yl and imidazol-5-yl, the latter being unsubstituted or bearing a (1-12C)alkyl group at the 1-position of the imidazole ring; and $R^3$ is hydroxy, a physiologically acceptable alcohol residue, or (1-4C)alkanesulphonamido;

or a pharmaceutically acceptable salt thereof. The compounds are thromboxane $A_2$ antagonists and inhibitors of thromboxane $A_2$ synthase.

8 Claims, No Drawings

HETEROCYCLIC ACIDS

This invention concerns novel heterocyclic acids containing alkenoic acid derivatives and, more particularly, it concerns novel 1,3-dioxan-5-yl alkenoic acids containing a particular heterocyclyl moiety attached at position 4 of the 1,3-dioxane ring. The alkenoic acids of the invention have valuable pharmaceutical properties and the invention includes pharmaceutical compositions containing the novel acids and processes for the manufacture and medical use of said novel acids.

It is known that the arachidonic acid metabolite thromboxane $A_2$ (hereinafter referred to as "$TXA_2$") is a powerful vasoconstrictor and a potent aggregator of blood platelets. $TXA_2$ is also a potent constrictor of bronchial and tracheal smooth muscle. $TXA_2$ may therefore be involved in a variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance. It may also be involved in asthma and inflammatory diseases such as arthritis.

It is believed that $TXA_2$ exerts its physiological action through the thromboxane receptor, via which receptor various other prostanoid contractile substances derived from arachidonic acid, such as prostaglandins $H_2$, $F_2$ alpha and prostaglandin $D_2$, can exert contractile effects. There are two principal ways in which the effects of $TXA_2$ can be ameliorated. The first way is to administer a pharmacological agent which possesses $TXA_2$ antagonist properties and the second is to administer a pharmacological agent which inhibits one or more of the enzymes involved in the production of $TXA_2$ and in particular which inhibits the enzyme known as thromboxane synthase ($TXA_2$ synthase). Accordingly, it may be seen that agents which possess both $TXA_2$ antagonist properties and $TXA_2$ synthase inhibitory properties may be expected to be of therapeutic value in the treatment of one or more of the above mentioned diseases or other diseases in which $TXA_2$ is involved.

In our co-pending European patent applications (Publication Nos. 329360 and 365328A2) there are described certain 4-pyridyl-1,3-dioxan-5-yl alkenoic acids which possess both $TXA_2$ antagonist and $TXA_2$ synthase inhibitory properties.

We have now discovered (and this is a basis for our invention) that, surprisingly, certain 1,3-dioxan-5-yl alkenoic acids of the formula I (set out, together with the other chemical structures, at the end of this specification) containing a particular thiazolyl or imidazolyl moiety attached to position 4 of the 1,3-dioxane ring have both significant $TXA_2$ antagonist properties and are good inhibitors of $TXA_2$ synthase.

According to the invention there is provided a 1,3-dioxane alkenoic acid derivative of the formula I (set out hereinafter together with the other chemical formulae in Roman numerals) wherein:
n is the integer 1 or 2;
Y is methyleneoxy, vinylene or ethylene;
$A^1$ is (1–6C)alkylene;
$R^1$ is a group of the formula $R^2.A^2$—, in which:
 $R^2$ is phenyl unsubstituted or bearing up to three substituents which are independently selected from (1–6C)alkyl, (1–6C)alkoxy, (2–6C)alkanoyl, (1–6C)alkylthio, (1–6C)alkylsulphonyl, halogeno, trifluoromethyl, nitro and cyano;
 $A^2$ is a direct bond to $R^2$ or a group of the formula —W—C($R^4$)($R^5$)— wherein W is oxygen, methylene or a direct bond to $R^2$, and $R^4$ and $R^5$ are independently (1–4C)alkyl;
Q is a heterocyclyl group selected from thiazol-5-yl and imidazol-5-yl, the latter being unsubstituted or bearing a (1–12C)alkyl group at the 1-position of the imidazole ring; and $R^3$ is hydroxy, a physiologically acceptable alcohol residue, or (1–4C)alkanesulphonamido;
or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$ and inhibiting the synthesis of $TXA_2$, it being well known in the art how to prepare individual optical isomers (for example by synthesis from optically active starting materials or resolution of a racemic form) and how to determine the $TXA_2$ antagonist properties and $TXA_2$ synthase inhibitory properties using one or more of the standard tests referred to hereinafter.

It will be understood that the groups at positions 2, 4 and 5 of the 1,3-dioxane moiety of formula I have cis-relative stereochemistry, as have the groups adjacent to Y when it is vinylene (i.e. the latter compoundd exist as the "Z" isomer). Further, although a particular configuration is shown in the chemical formulae attached hereto, this does not necessarily correspond to the absolute configuration.

It is to be understood that the generic term "alkylene" includes both straight chain and branched chain alkylene groups such as ethylene and ethylidene and other generic terms are to be construed similarly. However, when a specific term such as "butyl" is used, it is specific to the straight chain or "normal" butyl group, branched chain isomers such as "t-butyl" being referred to specifically when required.

Particular values for substituents which may be present on $R^2$ as defined above include, for example:
for (1–6C)alkyl: (1–4C)alkyl, such as methyl, ethyl, propyl, isopropyl, butyl, sec-butyl and t-butyl;
for (1–6C)alkoxy: (1–4C) alkoxy, such as methoxy, ethoxy, propoxy, isopropoxy, butoxy and t-butoxy;
for (2–6C)alkanoyl: acetyl;
for (1–6C)alkylthio: (1–4C)alkylthio, such as methylthio and ethylthio;
for (1–6C)alkylsulphonyl: (1–4C)alkylsulphonyl, such as methylsulphonyl and ethylsulphonyl;
for halogeno: fluoro, chloro and bromo;
Particular values for $R^3$ when it is a physiologically acceptable alcohol residue are those which render the subsequent ester biodegradable and are chosen from, for example, (1–6C)alkyl optionally bearing a hydroxy or (1–4C)alkoxy substituent, such as methyl, ethyl, 2-hydroxyethyl, 2-methoxyethyl, propyl or 3-hydroxypropyl; phenyl; and benzyl; the latter two of which may bear 1 or 2 optional substituents on the aromatic ring selected from halogeno (such as fluoro, chloro, bromo or iodo), (1–4C)alkyl (such as methyl or ethyl) and (1–4C)alkoxy (such as methoxy or ethoxy).

Particular values for $R^3$ when it is (1–4C)alkanesulphonamido include, for example, methanesulphonamido, ethanesulphonamido and butanesulphonamido.

Particular values for $A^1$ when it is (1–6C)alkylene include, for example: methylene, ethylene, trimethylene, 1,1-dimethylethylene, 1,1-dimethyltrimethylene, 2,2-dimethyltrimethylene and 1,2-dimethyltrimethylene, of which values ethylene and trimethylene are generally preferred, ethylene being particularly preferred.

A particular value for $R^4$ or $R^5$ is, for example, methyl, ethyl, propyl or butyl.

A particular value for a (1–12C)alkyl substituent which may be present on Q when it is an imidazol-5-yl group is, for example, (1–6C)alkyl, such as methyl, ethyl, propyl, butyl, pentyl or hexyl.

Q is preferably thiazol-5-yl, 1-methylimidazol-5-yl or 1-hexylimidazol-5-yl.

A preferred value for $A^2$ is, for example, a direct bond to $R^2$ or 1-oxy-1-methylethyl (i.e. a group of the formula —O—C(CH$_3$)$_2$—), it being understood that the oxy link is to the group $R^2$ and not to the 1,3-dioxane ring.

A preferred value for $R^1$ is, for example, 1-(4-methyl-2-nitrophenoxy)-1-methylethyl, 4-cyanophenyl, 1-(4-chloro-2-cyanophenoxy)-1-methylethyl, 1-(2-cyano-4-ethylphenoxy)-1-methylethyl, 1-(4-(1-methylethyl)-2-cyanophenoxy)-1-methylethyl, 1-(4-acetyl-2-nitrophenoxy)-1-methylethyl, 1-(2-trifluoromethylphenoxy)-1-methylethyl or 1-(4-methylthio-2-nitrophenoxy)-1-methylethyl.

A preferred value for $R^2$ is, for example, 4-methyl-2-nitrophenyl, 4-cyanophenyl, 4-chloro-2-cyanophenyl, 2-cyano-4-ethylphenyl, 4-(1-methylethyl)-2-cyanophenyl, 4-acetyl-2-nitrophenyl, 2-trifluoromethylphenyl, or 4-methylthio-2-nitrophenyl.

A generally preferred value for n is 1, for Y is cis-vinylene, for $A^1$ is ethylene and for $R^3$ is hydroxy.

A group of compounds of the invention of particular interest comprises compounds of the formula II wherein $A^3$ and $R^6$ have any of the meanings defined above for $A^1$ and $R^1$ respectively, and $R^3$ has any of the meanings defined above; together with the pharmaceutically acceptable salts thereof.

An especially preferred group of compounds of the invention of particular interest comprises compounds of the formula III wherein $A^4$ and $R^7$ have any of the meanings defined above for $A^1$ and $R^1$ respectively, and $R^3$ has any of the meanings defined above; together with the pharmaceutically acceptable salts thereof.

Particular novel compounds of the invention are described in the accompanying Examples and are provided, together with their pharmaceutically acceptable salts, as a further feature of the invention.

It will be appreciated that certain of the compounds of formula I can form salts with acids as well as bases. Particular pharmaceutically acceptable salts therefore include, for example, alkali metal and alkaline earth metal salts, ammonium salts, salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide, and also, for those compounds that are sufficiently basic, salts with acids affording physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be manufactured by conventional procedures of organic chemistry well known in the art for the manufacture of structurally analogous compounds. Such procedures are provided as a further feature of the invention and are illustrated by the following representative procedures in which $R^1$, $R^3$, Q, Y, $A^1$ and n have any of the meanings defined hereinbefore.

(a) A diol derivative of the formula IV wherein one of $T^1$ and $T^2$ is hydrogen and the other is hydrogen or a group of the formula —CRaRb.OH (wherein Ra and Rb are the same or different (1–4C) alkyl) is reacted with an aldehyde derivative of the formula $R^1$.CHO or an acetal, hemiacetal or hydrate thereof.

The latter aldehyde [or its hydrate, or is acetal or hemiacetal with a (1–4C)alkanol (such as methanol or ethanol)] may conveniently be present in an excess.

The reaction is generally performed in the presence of an acid such as hydrogen chloride, hydrogen bromide, sulphuric acid, phosphoric acid, methanesulphonic acid or p-toluenesulphonic acid, conveniently in the presence of a suitable solvent or diluent, such as acetonitrile, dichloromethane, toluene, xylene or an ether, for example, tetrahydrofuran, dibutyl ether, methyl t-butyl ether or 1,2-dimethoxyethane, and at a temperature in the range, for example, 0° to 80° C. It has been found to be particularly advantageous to heat the reactants under reflux in acetonitrile and then allow the acetonitrile to evaporate off, thereby allowing the temperature to rise to about 130° C.

Those starting materials of formula IV wherein $T^1$ and $T^2$ are both hydrogen may be obtained, for example, by mild, acid catalysed, hydrolysis or alcoholysis of the dioxane ring of a compound of formula V wherein one of Ra and Rb is hydrogen or (1–4C)alkyl (such as methyl or ethyl) and the other is (1–4C)alkyl, obtained by an analogous procedure to process (d) hereinbelow, for example as described in European Patent No. 94239. The hydrolysis or alcoholysis will normally be carried out at a temperature in range 10° to 80° C. using an aqueous mineral acid such as hydrochloric acid, or a sulphonic acid such as p-toluene sulphonic acid, in an alkanol such as methanol, ethanol or 2-propanol or an ether (such as tetrahydrofuran) as solvent.

The starting materials of formula IV wherein one of $T^1$ and $T^2$ is hydrogen and the other is a group of the formula —CRaRb.OH are intermediates in the above-mentioned formation of the starting materials of formula IV wherein $T^1$ and $T^2$ are both hydrogen. However, said intermediates are not normally isolated or characterised.

Accordingly, the invention also provides a preferred modified procedure (b) of process (a) which comprises reacting a 1,3-dioxane of formula V wherein one of Ra and Rb is hydrogen, methyl or ethyl and the other is methyl or ethyl with an excess of an aldehyde of the formula $R^1$.CHO (or a hydrate, acetal or hemiacetal thereof) in the presence of an acid (such as one of those given above), conveniently at a temperature in the range, for example, 10° to 80° C. and, optionally in the presence of a suitable solvent or diluent (such as one of those given above).

In some cases, it may be necessary to modify procedures (a) and (b) where the aldehyde of formula $R^1$.CHO is not particularly reactive or tends to form an acyclic hemiacetal when reacted with the compound of the formula IV or V. Thus, a further procedure (c) of the invention comprises reacting a compound of the formula IV wherein one of $T^1$ and $T^2$ is hydrogen and the other is alkanesulphonyl (especially methanesulphonyl) or arenesulphonyl (especially benzene- or toluenesulphonyl) with an aldehyde of the formula $R^1.CHO$ (or a hydrate, acetal or hemiacetal thereof) in the presence of an acid catalyst and under the same general conditions as given above for procedure (a), followed by base-catalysed cyclisation of the acyclic intermediate obtained, for example using an alkali metal carbonate or hydride such as potassium carbonate sodium hydride, in a suitable solvent or diluent (such as an ether described above) and at a temperature in the range, for example, 20°–50° C.

The necessary starting alkanesulphonyl or arenesulphonyl esters of formula IV defined above may be conveniently obtained from the corresponding diol of formula IV ($T^1=T^2=$hydrogen) by reaction with one molecular equivalent of the appropriate alkanesulphonyl or arenesulphonyl halide (such as methanesulphonyl chloride or p-toluenesulphonyl chloride) in a suitable solvent or diluent (such as an ether or dichloromethane) at or near ambient temperature and in the presence of a suitable base (such as triethylamine or pyridine).

(d) For those compounds of formula I in which Y is vinylene and $R^3$ is hydroxy, an aldehyde of the formula VI is reacted with a Wittig reagent of the formula: $R_3P=CH.A^1.CO_2^-M^+$ wherein R is (1–6C)alkyl or aryl (especially phenyl, which is preferred) and $M^+$ is a cation, for example an alkali metal cation such as the lithium, sodium or potassium cation.

The process in general produces the required compounds of formula I in which the substituents adjacent to the double bond have predominantly the preferred cis-relative stereochemistry i.e. as the "Z" isomer. However the process also produces generally small amounts of the analogous compounds having trans-relative stereochemistry (i.e. the "E" isomer) which may be removed by a conventional procedure such as chromatography or crystallisation.

The process may be conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C., but is conveniently performed at or near room temperature, for example in the range 0° to 35° C.

(e) For those compounds of formula I in which $R^3$ is hydroxy, an ester of the formula VII wherein $R^8$ is (1–6C)alkyl (especially methyl, ethyl, propyl or t-butyl), phenyl or benzyl the latter two optionally bearing 1 or 2 halogeno, (1–4C)alkyl or (1–4C)alkoxy substituents on the aromatic ring is decomposed.

The decomposition may be carried out using any one or more of the conventional reagents and conditions well known in the art for converting esters to acids. Thus, for example, the decomposition may conveniently be performed by base catalysed hydrolysis, for example by using an alkali metal hydroxide such as lithium, potassium or sodium hydroxide in an aqueous system conveniently in the presence of a suitable solvent or diluent such as tetrahydrofuran, methanol, ethanol or t-butyl methyl ether and a temperature in the general range, for example, 10° to 60° C. and, conveniently, at or near ambient temperature. Alternatively, when $R^8$ is t-butyl, the decomposition may be carried out thermally by heating the compound of formula VII at a temperature in the general range, for example, 80° to 150° C., alone or in the presence of a suitable diluent such as diphenylether or diphenylsulphone.

(f) For a compound of the formula I wherein Y is ethylene, a compound of the formula VIII wherein $Y^2$ is vinylene or ethynylene is hydrogenated.

The hydrogenation is preferably carried out in the presence of a suitable catalyst such as a noble metal catalyst, for example, palladium or platinum metal conveniently on an inert support such as carbon, barium sulphate, barium carbonate or calcium carbonate, using hydrogen at a pressure of about 1–2 bar. The process is generally carried out in a suitable sovent or diluent, for example, a (1–4C)alkanol (such as methanol, ethanol or propanol) and at a temperature in the range, for example, 15° to 35° C.

The invention also includes a modification of the above procedure adapted to the production of those compounds of formula I in which Y is vinylene which comprises partially hydrogenating a compound of the formula VIII in which $Y^2$ is ethynylene. In this modification, a suitable poisoned catalyst for example a Lindlar catalyst (such as palladium on calcium carbonate, poisoned with lead) is used with similar solvents and temperatures as in process (f).

(g) For a compound wherein Y is methyleneoxy, an alcohol of the formula IX is reacted with an alkanoic acid derivative of the formula X in which L is a leaving group for example halogeno (such as chloro, bromo or iodo), alkanesulphonyloxy (such as methanesulphonyloxy) or arenesulphonyloxy (such as benzene- or toluene-sulphonyloxy).

The process is preferably carried out in the presence of a suitable base, for example, an alkali metal alkoxide (such as sodium methoxide or ethoxide), hydride (such as sodium hydride) or alkane derivative (such as butyl lithium) and in a suitable solvent or diluent, for example in a (1–4C)alkanol when an alkali metal alkoxide is used, in N,N-dimethylformamide or an ether, such as tetrahydrofuran or t-butyl methyl ether, when an alkali metal hydride is used, or in an ether when an alkane derivative is used. The process is generally carried out at a temperature in the range, for example, 0° to 50° C. In many cases it is preferred to preform a salt of the alcohol of formula IX by reaction with the appropriate base and then react this salt with the alkanoic acid derivative of the formula X in a suitable solvent or diluent such as one of those referred to above.

The necessary starting materials for use in the above processes (a)–(g) may be obtained by general procedures well known for the production of structurally related compounds, for example using analogous procedures to those described in European patent no. 94239B1 and patent application publication no. 98690A2. The aldehydes of the formula VI may be obtained, for example, from the corresponding allyl compounds of the formula XI, itself obtained from a compound of the formula XII, as shown in Scheme 2 hereinafter and as illustrated in the Examples. The compounds of the formula XII may be obtained, for example, from an aldehyde of the formula Q.CHO or ester of the formula Q.CO.O.R wherein R is a (1–4C)alkyl group, as shown in Scheme 1. Compounds of the formula XII wherein Q is 5-thiazolyl or 5-imidazolyl, the latter of which optionally bearing an alkyl group at the 1-position, may be obtained as shown in Schemes 3 and 4 respectively. Alternatively, when a particular enantiomer is required, it may be obtained starting from a specific enantiomer of an oxazolidin-2-one of the formula XIII in which $R^9$ is (1-4C)alkyl (especially isopropyl) itself obtained from aldol condensation of the corresponding 3-(4-pentenoyl)oxazolidin-2-one with an aldehyde of the formula Q.CHO, as shown in Scheme 5 hereinafter.

The esters of formula VII may be made, for example, by carrying out process (a) using the appropriate ester of the diol corresponding to formula IV. Those compounds of formula VIII in which $Y^2$ is ethynylene may be made, for example, as shown in Scheme 6 hereinafter. The alcohols of formula IX may be obtained from the corresponding allyl compounds of formula XI (to give the IX compounds in which n=2) by conventional hydroboration (boron hydride, followed by treatment with hydrogen peroxide) or by reduction of the corresponding aldehydes (for example sodium borohydride) of formula VI, for example, as indicated in Scheme 2 (to give the X compounds in which n=1).

The aldehydes of the formula $R^1$.CHO which are new may be made, by conventional procedures well known in the art, for example those described in European Patent Application, Publication No. 365328. The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (d) above.

It will be understood that the compounds of formula I wherein $R^3$ is hydroxy may also be obtained by other conventional procedures well known in the art, for example by base catalysed hydrolysis of the corresponding amides or nitriles. In addition, those compounds of formula I wherein $R^3$ is other than hydroxy may be made by conventional esterification or sulphonamidation procedures from the compounds wherein $R^3$ is hydroxy (or a reactive derivative thereof) and the appropriate alcohol, phenol or (1-4C)alkanesulphonamide. Such procedures are also within the ambit of the invention.

Whereafter, when a salt of a compound of formula I is required, it may be obtained by reaction with the appropriate base or acid affording a physiologically acceptable ion, or by any other conventional salt formation procedure.

Further, when an optically active form of a compound of formula I is required, one of the aforesaid processes may be carried out using an optically active starting material (for example as described in Examples 2 and 12). A particularily preferred process starts from an optically active compound of formula IV in which $T^1$ and $T^2$ are both hydrogen.

Optically active compounds of formula IV in which $T^1$ and $T^2$ are both hydrogen may be obtained by reacting a compound of formula XIV in which $R^{10}$ is a (1-6C)alkyl group (such as methyl, ethyl, propyl, isopropyl or butyl, especially isopropyl) or phenyl(1-4C)alkyl group (such as benzyl) and $R^{11}$ is a hydrogen atom or a phenyl group, with a selective reducing agent such as sodium borohydride. The reaction is conveniently performed in the presence of a solvent such as an alcohol, for example methanol, at a temperature in the range of from −10° to 50° C., preferably from −5° to 10° C.

The compounds of formula XIV may be prepared by reacting a compound of formula XV with a carboxaldehyde of formula QCHO in the presence of a dialkylboryl sulphonate (such as diethyl- or dibutylboryl trifluoromethylsulphonate) and a tertiary amine such as diisopropylethylamine. The reaction is conveniently performed in the presence of a suitable solvent such as a halogenated hydrocarbon, for example dichloromethane, at a temperature in the range of from −80° to 15° C., preferably from −10° to 10° C.

The compounds of formula XV may be prepared by reacting a compound of formula XVI in which M is an alkali metal atom (such as lithium) with a compound of formula XVII in which $R^{3'}$ is an alcohol residue (such as a (1-6C)alkyl group, for example methyl or ethyl, a phenyl group or a benzyl group), or a reactive derivative thereof (such as a halide, for example for chloride). The reaction is conveniently performed at a temperature in the range of from −80° to 30° C., and in the presence of a solvent such as tetrahydrofuran.

The compounds of formula XVII may be prepared from cyclooctadiene, for example following the method described in H. Klunenberg and H. J. Schafer, Angew. Chem. Int. Ed. Engl., (1978), 17, 47. Compounds of formula XVI may be prepared by reacting the corresponding compound of formula XVI in which M is hydrogen with a strong alkali metal base, such as butyl lithium. These compounds of formula XVI are commercially available.

The process described above for the preparation of optically active compounds of formula IV from compound of formula XVII has been found to be particularily advantageous. Thus it has been found to afford compounds of formula IV in the form of a substantially pure enantiomer, and in high yield, based upon the expensive chiral reagent of formula XVI. Furthermore, it will be appreciated that this process can easily be adapted for the preparation of optically active compounds of the aforementioned EP 329360 and EP 365328 by using a pyridine carboxaldehyde in place of a compound of formula QCHO. The intermediates of formula XV are therefore particularily advantageous, and form a further aspect of the present invention.

Alternatively, the racemic form of a compound of formula I may be reacted with an optically active form of a suitable organic acid or base, for example, camphorsulphonic acid, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid (or base) using a conventional procedure, for example using an aqueous mineral acid such as dilute hydrochloric acid (or aqueous alkali such as aqueous sodium hydroxide).

Many of the intermediates defined herein are novel, for example those of formulae IV, V, VI, VII, VIII and IX, and are provided as further, separate features of the invention.

As stated earlier, the compounds of formula I possess significant $TXA_2$ antagonist properties and are inhibitors of $TXA_2$ synthase. The $TXA_2$ antagonism may be demonstrated in one or other of the following standard tests:

(a) The rat aortic strip model analogous to that devised by Piper and Vane (*Nature*, 1969, 223, 29-35) using as agonist the $TXA_2$ mimetic agent known U46619 (described by R. L. Jones et alia in "Chemistry, Biochemistry and Pharmacological Activity of Prostanoids" edited by S. M. Roberts and F. Scheinmann, at page 211; Pergamon Press, 1979);

(b) a blood platelet aggregation test based on that described by Born (*Nature*, 1962, 194, 927-929) and involving:

(i) aggregating human, citrated, platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range $10^{-5}M$ to $10^{-10}M$); and (iii) calculating a $pA_2$ value indicating potency of $TXA_2$ antagonism for the test compound, averaged over several concentrations, from the calculated 50% response value for U46619 aggregation in the presence and absence of test compound; or (c) a bronchoconstriction test involving measuring the inhibition by a test compound of the bronchoconstriction induced in Konzett-Rossler, anaesthetised guinea-pig model (as modified by Collier and James, *Brit.J.Pharmacol.*, 1967, 30, 283-307) by intravenous administration of the $TXA_2$ mimetic agent, U46619, which involves:

(i) obtaining a cumulative dose-response curve to U46619 induced bronchoconstriction by intravenous administration of constant volumes of increasing concentrations of U46619 (0.2-4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

Test (b) may conveniently be modified to demonstrate the antagonism of the effects of $TXA_2$ in vivo by assessing the effects of a test compound on the aggregation of blood platelets obtained after administration of test compound to a laboratory animal, such as a rabbit, rat, guinea pig or dog. However, when the aggregation of dog platelets is being studied it is necessary to use a predetermined, threshold concentration of the platelet aggregation agent adenosine diphosphate (about $0.4-1.2\times 10^{-6}M$) together with the $TXA_2$ mimetic agent, U46619.

The antagonism of the effects of $TXA_2$ on the vasculature may also be demonstrated, for example in rats in the following procedure:

(d) Male rats (Alderley Park strain) are anaesthetised with sodium pentobarbital and blood pressure is monitored at the carotid artery. The $TXA_2$ mimetic agent U46619 is administered intravenously at 5 μg/kg via the jugular vein to produce 20-30 mm/Hg (2640-3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

The $TXA_2$ synthase inhibitory properties of a test compound may be demonstrated using the standard in vitro test procedure [test (e)] described by Howarth et alia (*Biochem. Soc. Transactions*, 1982, 10, 239-240) using a human platelet microsomal $TXA_2$ synthase preparation and using a quantitative thin layer radiochromatographic method to assess the conversion of $[1-^{14}C]$arachidonic acid to the $TXA_2$ metabolite thromboxane $B_2$ ($TXB_2$).

The $TXA_2$ synthase inhibitory properties of a test compound may also be demonstrated in a standard procedure [test (f)] involving obtaining blood samples from laboratory animals (typically rats, but also guinea pigs, rabbits or dogs) dosed with the test compound, generally by the oral route. The samples treated with anticoagulant are first incubated at 37° C. with collagen (at about 100 micro M final concentration), then mixed with the cyclooxygenase inhibitor indomethacin (at about $10^{-3}M$), centrifuged and the level of the $TXA_2$ metabolite, $TXB_2$, determined by a standard radioimmunoassay technqiue. By comparison of the amount of $TXB_2$ present in the plasma from animals dosed with test compound with that in the plasma of a control group dosed with placebo, the $TXA_2$ synthase inhibitory properties may be assessed.

In general, the majority of compounds of formula I wherein $R^3$ is hydroxy show effects in the following ranges in one or more of the above tests:

test (a): $pA_2$ of $>5.5$
test (b): $PA_2$ of $>5.5$
test (c): dose ratio of $>5$, 1 hour after dosing at 10 mg/kg
test (d): significant inhibition of U46619 induced hypertension for at least 1 hour following oral dosing at 50 mg/kg or less
test (e): $IC_{50}$ of $<1.0\times 10^{-6}M$
test (f): significant inhibition of $TXB_2$ production 1 hour following a dose of 100 mg/kg or less.

No overt toxic or other untoward effects are generally observed with representative compounds of formula I having effects in in vivo tests (c), (d) or (f) at several multiples of the minimum effective dose.

In general, compounds of formula I wherein $R^3$ is other than hydroxy show lower activity in the above in vitro tests but show similar activity to the compounds of formula I in which $R^3$ is hydroxy in the in vivo tests.

The compound described in Example 2 hereinafter possesses both $TXA_2$ antagonist and $TXA_2$ synthase inhibitory properties as indicated by a $pA_2$ of 8.11 in test (b) and an $IC_{50}$ of $1.6\times 10^{-8}M$ in test (e).

In addition to the aforementioned properties, certain of the compounds of the invention exhibit a particularly marked selectivity for the inhibition of thromboxane synthase compared with prostacyclin synthase. A consequence of the inhibition of $TXA_2$ synthase inhibition is inter alia the accumulation of prostaglandin $H_2$, which is then available for metabolic conversion by the action of the enzyme prostacyclin synthase to prostacyclin $PGI_2$. The action of $PGI_2$ plays an important role in preventing blood platelet aggregation and vasoconstriction. Therefore it is important that an agent possessing $TXA_2$ antagonist and synthase inhibitory properties selectively inhibits $TXA_2$ synthase compared with prostacyclin synthase.

The prostacyclin synthase inhibitory properties of a test compound may be demonstrated in a standard procedure [test (g)] involving obtaining cultured human endothelial cells from unbilical vein which are then seeded into multiwell plates ($5 \times 10^{-4}$ cells/well) and allowed to grow to 70-80% confluence at 37° C. under an atmosphere of 5% carbon dioxide in air. The growth medium is aspirated from the wells and the endothelial cell monolayers are washed twice with alquots of medium (1 ml, Earls 199 medium) containing vehicle or compound. The monolayers are first incubated with medium containing vehicle or compound for 30 minutes at 37° C. Arachidonic acid (10 micro M) is added to the medium and the monolayers are incubated for a further 2 hours with a fresh aliquot of medium. The incubation is terminated by aspiration of the medium into indomethacin (1 micro M). The sample is stored at $-20°$ C. and radioimmunoassay for the stable metabolite 6-oxoPGF1a is performed. By comparison of the amount of 6-oxoPGF1a present in a sample incubated in the presence of compound to one incubated in the absence of compound, the prostacyclin synthase inhibitory properties of the compound may be assessed. Compounds exhibiting an $IC_{50}$ of greater than 100 micro M are deemed to have no significant prostacyclin synthase inhibitory properties.

In test (g), certain of the compounds of the invention have an $IC_{50} > 100 \times 10^{-6}M$. For example, the compound described in Example 2 hereinafter exhibits no significant prostacyclin inhibitory properties as indicated by an $IC_{50}$ of 210.7 in test (g).

As stated previously, by virtue of their combined $TXA_2$ antagonist and $TXA_2$ synthase inhibitory properties, the compounds of formula I may be used in the therapy or prevention of diseases or adverse conditions in warm-blooded animals in which $TXA_2$ (or prostaglandins $H_2$, $D_2$ and/or $F_2$ alpha) are involved. In general, a compound of formula I will be administered for this purpose by an oral, rectal, intravenous, subcutaneous, intramuscular or inhalation route, so that a dose in the range, for example 0.01-15 mg/kg body weight, will be given up to four times per day, varying with the route of administration, the severity of the condition and the size and age of the patient under treatment.

The compounds of formula I will generally be used in the form of a pharmaceutical composition comprising a compound of formula I or, a pharmaceutically acceptable salt thereof as defined hereinabove, together with a pharmaceutically acceptable diluent or carrier. Such a composition is provided as a further feature of the invention and may be in variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, thrombolytic agent (such as streptokinase), beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition. Still further, a known $TXA_2$ antagonist, such as a preferred compound described in European patent application, Publication No. 201354, or a known $TXA_2$ synthase inhibitor such as dazoxiben or furegrelate [U63557] may be present in addition to a compound of the formula I, or a pharmaceutically acceptable salt thereof, in a composition according to the invention in order to modify the overall balance of $TXA_2$ antagonist and $TXA_2$ synthase inhibitory effects for the required therapeutic effect in any of the aforesaid diseases or disease conditions.

In addition to their use in therapeutic medicine, the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist and synthase inhibitory properties in helping to maintain the viability of blood and blood vessels in warm-blooded animals (or parts thereof) under-going artificial extracorporeal circulation, for example during limb or organ transplants. When used for this purpose a compound of formula I, or a physiologically acceptable salt thereof, will generally be administered so that a steady state concentration in the range, for example, 0.1 to 10 mg. per liter is achieved in the blood.

The invention will now be illustrated by the following non-limiting Examples in which unless otherwise stated:

(i) concentrations and evaporations were carried out by rotary evaporation in vacuo;

(ii) operations were carried out at room temperature, that is in the range 18°-26° C.;

(iii) flash column chromatography was carried out on silica (Merck Art. 7734) and column chromatography on silica (Merck Art. 9385) both available from E Merck and Co., Darmstadt, West Germany;

(iv) yields are given for illustration only and are not necessarily the maximum attainable by diligent process development;

(v) proton NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) THF refers to tetrahydrofuran dried by distillation from lithium aluminium hydride under an atmosphere of argon; ether refers to diethyl ether.

EXAMPLE 1

1M Aqueous sodium hydroxide solution (2 ml) was added to a solution of methyl 4(Z)-6-[(2,4,5-cis)-2-(1-(4-methyl-2-nitrophenoxy)-1-methylethyl)-4-(5-thiazolyl)-1,3-dioxan-5-yl]hexenoate (G) (0.120 g) in methanol (5 ml) and the mixture was stirred at ambient temperature for 5 hours. Saturated aqueous ammonium chloride solution (2 ml) was added and the mixture was extracted three times with ethyl acetate. The combined extracts were dried (MgSO4) and concentrated. The residue was purified by column chromatography, eluting with 10% methanol/dichloromethane (v/v), to give 4(Z)-6-[(2,4,5-cis)-2-(1-(4-methyl-2-nitrophenoxy)-1-methylethyl)-4-(5-thiazolyl)-1,3,-dioxan-5-yl]hexenoic acid (0.087 g; 76% yield) as an oil; NMR: 1.4(6H,s), 1.65–1.85(2H,m), 2.20–2.55(8H,m), 3.85–4.15(2H,m), 4.79(1H,s), 5.22–5.52(3H,m), 7.14–7.26(2H,m), 7.49(1H,s), 7.69(1H,m), 8.76(1H,m); m/e 477 (M+H)+.

The starting material G was prepared as follows:

(i) Ethyl pent-4-enoate (14.3 g) was added dropwise to a solution of lithium diisopropylamide (THF complex, 1.5M solution in cyclohexane) (75.1 ml) in THF (250 ml) at −78° C. under an atmosphere of argon. After stirring the mixture for 1 hour at this temperature, a solution of 2-tert-butyldimethylsilylthiazole-5-carboxaldehyde (R) (23.25 g) in THF (50 ml) was added. The mixture was allowed to warm to ambient temperature over 1 hour, and then quenched at −10° C. with excess saturated aqueous sodium bicarbonate solution. The mixture was extracted three times with ether, and the combined extracts were dried (K2CO3) and concentrated. The residue was purified by column chromatography on alumina, eluting first with ethyl acetate and then with 10% methanol/dichloromethane (v/v), to give ethyl (2RS)-2-[(1RS)-1-hydroxy-1-(5-[2-tert-butyldimethylsilyl]thiazolyl)methyl]pent-4-enoate (A) (32.2 g; 88% yield) as an oil; NMR: 0.32(6H,s), 0.93(9H,s), 1.05–1.30(3H,m), 2.27–2.62(2H,m), 2.86(1H,m), 4.0–4.2(2H,m), 4.95–5.33(3H,m), 5.72(1H,m), 7.91(1H,s).

(ii) A solution of compound A (32.4 g) in THF (25 ml) was added to a suspension of lithium aluminium hydride (7.0 g) in THF (75 ml) at 0° C. with stirring under an atmosphere of argon. The mixture was allowed to warm to ambient temperature over 2 hours. A saturated aqueous solution of sodium carbonate (10 ml) was added slowly dropwise and the mixture was stirred for 1 hour. The mixture was filtered through a pad of diatomaceous earth and the pad was washed well with ethyl acetate. The filtrate was concentrated and the residue purified by column chromatography, eluting with ethyl acetate, to give (1RS,2RS)-2-allyl-1-(5-[2-tert-butyldimethylsilyl]thiazolyl)-1,3-propanediol (B) (20.0 g; 70% yield) as an oil; NMR: 0.36(6H,s), 0.94(9H,s), 2.0–2.2(3H,m), 2.55(1H,broad s), 2.90(1H, broad s), 3.6–3.95(2H,m), 4.95–5.32(3H,m), 5.73(1H,m), 7.89(1H,s).

(iii) p-Toluenesulphonic acid monohydrate (13.4 g) was added to a solution of compound B (20.0 g) in 2,2-dimethoxypropane (100 ml) and the mixture was stirred for 18 hours at ambient temperature. A 1M solution of tetrabutylammonium fluoride in THF (150 ml) was then added and the mixture stirred for a further 15 minutes. The reaction mixture was then neutralised with excess saturated aqueous sodium bicarbonate solution and extracted three times with ethyl acetate. The combined extracts were dried (MgSO4) and concentrated and the residue was purified by column chromatography, eluting with 25% ethyl acetate/hexane (v/v), to give (4RS,5RS)-5-allyl-2,2-dimethyl-4-(5-thiazolyl)-1,3-dioxane (C) (13.0 g; 85% yield) as an oil; NMR: 1.45–1.55(6H,m), 1.6–2.05 and 2.4–2.5(3H,m), 3.68–4.16(2H,m), 4.9–5.1 and 5.5–5.72(4H,m), 7.72 and 7.81(isomers,1H,2s), 8.72 and 8.79(isomers, 1H,2s).

(iv) Ozone (1.3 g) in oxygen was bubbled through a solution of compound C (5.65 g) in methanol (80 ml) at −78° C. Argon was then bubbled through the solution to discharge excess ozone and dimethyl sulphide (12 ml) was added. The solution was allowed to warm to ambient temperature and concentrated. The residue was purified by column chromatography, eluting with ethyl acetate, to give 2,2-dimethyl-4-(5-thiazolyl)-1,3-dioxan-cis-5-yl-acetaldehyde (D) (as the less polar isomer) (2.97 g; 53% yield) as a solid, m.p. 86°–89° C.; NMR: 1.5(3H,s), 1.57(3H,s), 2.35–2.47(2H,m), 3.0(1H,m), 3.79(1H,m), 4.25(1H,m), 5.52(1H,m), 7.72(1H,s), 8.74(1H,s), 9.70(1H,s).

(v) A solution of compound D (0.42 g) in THF (5 ml) was added under argon to a stirred, ice-cooled solution of the yield prepared from (3-carboxypropyl)triphenylphosphonium bromide (1.9 g) and potassium tert-butoxide (0.97 g) in THF (30 ml). The mixture was stirred for 16 hours at ambient temperature, then cooled to 5° C. and excess water was added. After extracting three times with ethyl acetate, the combined extracts were dried (MgSO4) and concentrated. Ether was added to the residue, insoluble material removed by filtration, and the filtrate was concentrated. The residue was purified by column chromatography, eluting with 10% methanol/dichloromethane (v/v), to give 4(Z)-6-[2,2-dimethyl-4-(5-thiazolyl)-1,3-dioxan-cis-5-yl]hexenoic acid (E) (0.35 g; 68% yield) as an oil; NMR: 1.49(3H,s), 1.53(3H,s), 1.5–2.7(7H,m), 3.82(1H,dd,J=12,1.5 Hz), 4.11(1H,dm,J=12 Hz), 5.2–5.6(3H,m), 7.75(1H,s), 8.77(1H,s); m/e 312 (M+H)+; mass measurement 312.1258; theory 312.1270.

(vi) p-Toluenesulphonic acid monohydrate (0.264 g) was added to a solution of compound E (0.36 g) in methanol (5 ml) and the solution was stirred at ambient temperature for 1 hour. Excess saturated aqueous sodium bicarbonate solution was added and the mixture extracted three times with ethyl acetate. The combined extracts were dried (MgSO4) and concentrated to give methyl 4(Z)-erythro-8-hydroxy-7-hydroxymethyl-8-(5-thiazolyl)-4-octenoate (F) (0.3 g, 80% yield) as an oil which was used without further purification; NMR: 1.5–2.7(7H,m), 2.95(1H,broad s), 3.68(3H,s), 3.7–4.0(2H,m), 5.27–5.5(3H,m), 7.78(1H,s), 8.76(1H,s); m/e 286 (M+H)+.

(vii) p-Toluenesulphonic acid monohydrate (0.105 g) was added to a solution of compound F (0.143 g), 2-(4-methyl-2-nitrophenoxy)-2-methylpropanal (prepared as in European Patent Application, Publication No. 365328) (0.167 g), and trimethylorthoformate (0.106 g) in acetonitrile (2 ml), and the mixture was stirred at reflux for 3 hours. The condenser was removed and the mixture heated at 140° C. for 30 minutes. The mixture was cooled and diluted with ethyl acetate (5 ml). Saturated aqueous sodium biacarbonate solution (5 ml) was added, and the layers separated. The aqueous phase was extracted three times with ethyl acetate. The combined organic phases were dried (MgSO4) and concentrated to give an oil which was purified by column chromatography, eluting first with 25% ethyl acetate/hexane (v/v) and then ethyl acetate to give methyl 4(Z)-6-

[(2,4,5-cis)-2-(1-(4-methyl-2-nitrophenoxy)-1-methylethyl)-4-(5-thiazolyl)-1,3-dioxan-5-yl]hexenoate (G) (0.120 g; 49% yield) as an oil; NMR: 1.40(3H,s), 1.42(3H,s), 1.6–1.85(2H,m), 2.25–2.55(10H,m), 3.62(3H,s), 3.85–4.15(2H,m), 4.80(1H,s), 5.2–5.55(3H,m), 7.1–7.25(2H,m), 7.48(1H,s), 7.68(1H,s), 8.73(1H,s); m/e 491 (M+H)+.

2-tert-Butyldimethylsilylthiazole-5-carboxaldehyde (compound R), used in Example 1, part (i) was obtained as follows:

(a) A solution of 2-bromothiazole (57.4 g) in ether (70 ml) was added slowly to a solution of n-butyllithium (1.6M solution in hexane, 241 ml) in ether (700 ml) under an atmosphere of argon, maintaining the temperature below −60° C. After stirring for 1 hour at −70° C., a solution of tert-butylchlorodimethylsilane (63.0 g) in ether (70 ml) was added slowly dropwise. The reaction mixture was then allowed to warm to ambient temperature and stirred for 16 hours. Saturated aqueous sodium bicarbonate solution was added, the layers were separated, and the aqueous phase extracted twice with ether. The combined organic phases were dried (MgSO4), concentrated, and the residue was purified by column chromatography, eluting with 25% ethyl acetate/hexane (v/v), and subsequent distillation to give 2-tert-butyldimethylsilylthiazole (Q) (46 g, 58% yield) as an oil (b.p. 88°–96° C. at 10 mm of mercury); NMR: 0.38(6H,s), 0.97(9H,s), 7.51(1H,d). 8.12(1H,d).

(b) A solution of compound Q (40 g) in ether (100 ml) was added dropwise to a solution of n-butyllithium (1.6M solution in hexane, 138 ml) in ether (300 ml) at −70° C. under an atmosphere of argon. The mixture was stirred for 1 hour at this temperature and then N,N-dimethylformamide (30 ml) was added dropwise. The mixture was stirred for 30 minutes at −70° C., then warmed to −40° C. Excess saturated aqueous ammonium chloride solution was added and the mixture allowed to warm to ambient temperature. The layers were separated and the aqueous phase extracted three times with ether. The organic phases were combined, dried (MgSO4), and concentrated. The residue was purified by column chromatography, eluting with 25% ethyl acetate/hexane (v/v), to give 2-tert-butyldimethylsilylthiazole-5-carboxaldehyde (R) (31 g, 69% yield) as an oil; NMR: 0.32(6H,s), 0.89(9H,s), 8.55(1H,s), 10.0(1H,s).

The intermediate compound E used in Example 1, part (vi) above was also obtained as follows:

(a) Sodium borohydride (0.15 g) was added to an ice-cooled solution of methyl 4(Z)-8-oxooctenoate (0.468 g) (prepared by ozonolysis of 1,5-cyclooctadiene by the method of Schreiber, Tet. Lett., 1982, 23, 3867) in methanol (3 ml). After stirring for 2 hours, the solution was poured into water and extracted three times with ether. The combined extracts were dried (MgSO4) and concentrated to give methyl 4(Z)-8-hydroxyoctenoate (L) (0.46 g) as an oil; NMR: 1.55–1.72(2H,m), 2.0–2.2(2H,m), 2.4(4H,m), 3.4–3.52(5H,m), 5.3–5.5(2H,m).

(b) Triethylamine (0.46 ml) was added to a solution of the alcohol L (0.46 g) in dichloromethane (10 ml) at 0° C., followed by tert-butylchlorodimethylsilane (0.5 g) and 4-dimethylaminopyridine (0.03 g). After stirring at ambient temperature for 16 hours, the mixture was concentrated and the residue purified by column chromatography, eluting with 25% ethyl acetate/hexane (v/v), to give methyl 4(Z)-8-tert-butyldimethylsiloxyoctenoate (M) (0.54 g, 83% yield) as an oil; NMR: 0.02(6H,s), 0.9(9H,s), 1.48–1.64(2H,m), 2.0–2.2(2H,m), 2.35–2.4(4H,m), 3.62(2H,t), 3.69(3H,s), 5.3–5.5(2H,m).

(c) Using an analogous procedure to that described in part (i) above, but using compound M in place of ethyl pent-4-enoate, there was obtained methyl 4(Z)-(2RS)-8-tert-butyldimethylsiloxy-2-[(1RS)-1-hydroxy-1-(5-[2-tert-butyldimethylsilyl]thiazolyl)]methyloctenoate (N) (34% yield) as an oil; NMR: 0.0(6H,s), 0.35(6H,s), 0.85(9H,s), 0.92(9H,s), 1.2–1.6(6H,m), 2.0(1H,m), 3.5–3.6(5H,m), 5.2–5.5(3H,m), 7.88(1H,s); m/e 514 (M+H)+.

(d) Using an analogous reduction procedure to that described in part (ii) above, but using compound N as starting material, there was obtained (1RS,2RS)-2-[2(Z)-6-tert-butyldimethylsiloxyhexenyl]-1-[5-(2-tert-butyldimethylsilyl)thiazolyl]-1,3-propanediol (compound 0) (91% yield) as an oil; NMR: 0.02(6H,s), 0.46(6H,s), 0.88(9H,s), 0.95(9H,s), 1.2–2.3(7H,m), 3.59(2H,m), 3.72(2H,m), 5.25–5.5(3H,m), 7.9(1H,s).

(e) p-Toluenesulphonic acid monohydrate (0.456 g) was added to a solution of compound 0 (1.0 g) in 2,2-dimethoxypropane (15 ml) and the mixture stirred for 2 hours. Excess saturated aqueous sodium carbonate solution was then added and the mixture concentrated. The residue was partitioned between water and ether and the aqueous phase extracted three times with ether. The combined organic phases were dried (MgSO4) and concentrated. The residue was dissolved in acetic acid (5 ml) and stirred for 3 hours. Excess saturated aqueous sodium bicarbonate solution was added and the mixture extracted three times with ether. The combined extracts were dried (MgSO4), concentrated, and the residue purified by column chromatography, eluting with ethyl acetate, to give 4(Z)-6-[2,2-dimethyl-4-(5-thiazolyl)-1,3-dioxan-cis-5-yl]hexenol (P) (0.34 g) as an oil; NMR: 1.51(3H,s), 1.55(3H,s), 1.56–2.4(6H,m), 2.67(1H,m), 3.6(2H,m), 3.86(1H,m), 4.12(1H,m), 5.2–5.6(3H,m), 7.76(1H,s), 8.73(1H,s); m/e 298 (M+H)+.

(f) Pyridinium dichromate (1.0 g) was added to a solution of compound P (0.23 g) in N,N-dimethylformamide (3 ml) and the mixture was stirred for 16 hours. The mixture was then poured into a large excess of water and extracted five times with dichloromethane. The combined extracts were dried (MgSO4), concentrated, and the residue was purified by column chromatography, eluting with 10% methanol/dichloromethane (v/v), to give 4(Z)-6-[2,2-dimethyl-4-(5-thiazolyl)-1,3-dioxan-cis-5-yl]hexenoic acid (E) (0.035 g) as an oil; NMR and mass spectral data identical to that of the product obtained in part (v) above.

EXAMPLE 2

Using a similar procedure to that described in Example 1, but starting from methyl 4(Z)-6-[(2S,4S,5R)-2-(1-(4-methyl-2-nitrophenoxy)-1-methylethyl)-4-(5-thiazolyl)-1,3-dioxan-5-yl]hexenoate (H), there was obtained 4(Z)-6-[(2S,4S,5R)-2-(1-(4-methyl-2-nitrophenoxy)-1-methylethyl-4-(5-thiazolyl)-1,3-dioxan-5-yl]hexenoic acid as a foam; NMR amd mass spectral data was similar to that of the racemic material described in Example 1; $^{20}[\alpha]_D$ −55.3° (c 1.0, ethanol).

The starting ester H was obtained using an analogous procedure to that described in Example 1, parts (ii)–(vii) but using, as starting material in part (ii) instead of compound A, methyl (2S)-2-[(1S)-1-hydroxy-1-(5-[2-tert-butyldimethylsilyl]thiazolyl)methyl]pent-4-enoate (K). Compound K was obtained as follows:

(i) A 1.53M solution of butyllithium in hexane (23.9 ml) was added to a solution of 4S-(−)-4-isopropyl-2-oxazolidinone (4.68 g) in THF (75 ml) cooled to −78° C. under argon. The mixture was then allowed to warm to −50° C. and stirred for 30 minutes. The mixture was then recooled to −78° C. and a solution of 4-pentenoyl chloride (4.33 g) in THF (10 ml) was added dropwise. After the addition, the mixture was stirred at −78° C. for 30 minutes, and then allowed to warm to −20° C. Saturated aqueous ammonium chloride solution (20 ml) was added and the mixture extracted with ethyl acetate (3 × 100 ml). The combined organic phases were dried (MgSO$_4$) and concentrated. The residue was purified by flash chromatography, eluting with 20% ethyl acetate/hexane (v/v), to give (4S)-4-isopropyl-3-(4-pentenoyl-)oxazolidin-2-one (I) (6.34 g) as an oil; NMR: 0.85–0.95(6H,m), 2.3–2.5(3H,m), 2.9–3.2(2H,m), 4.15–4.5(3H,m), 4.95–5.15(2H,m), 5.75–6.0(1H,m).

(ii) A 1M solution of dibutylboron triflate in dichloromethane (102.4 ml) was added to a solution of compound I (19.7 g) in dry dichloromethane (400 ml) at 5° C. under argon, followed by diisopropylethylamine (19.6 ml). The reaction mixture was stirred at 5° C. for 30 minutes and then cooled to −78° C. A solution of 2-tert-butyldimethylsilylthiazole-5-carboxaldehyde (R) (23.2 g) in dry dichloromethane (40 ml) was added dropwise. The mixture was then stirred for 30 minutes at −78° C., and then allowed to warm to −50° C. over 30 minutes. The cooling bath was removed and the reaction mixture was stirred at ambient temperature for 2 hours. The mixture was then cooled to 5° C. and pH 7.2 phosphate buffer solution (80 ml) was added, followed by hydrogen peroxide (17 ml, 30% w/v aqueous solution). The mixture was stirred for 30 minutes and then poured into water and extracted three times with dichloromethane. The combined extracts were dried (MgSO$_4$) and evaporated. The semi-solid residue which formed on standing at ambient temperature was triturated with hexane and the hexane liquors were concentrated. The residue was purified by column chromatography, eluting with ethyl acetate/hexane (10% v/v, gradually increasing to 50%), to give (4S)-(3-[(2S)-2-[(1S)-1-hydroxy-1-(4-[2-tert-butyldimethylsilyl]-thiazolyl)methyl]pent-4-enoyl)-4-isopropyloxazolidin-2-one (J) (35.5 g) as an oil; NMR: 0.36(6H,s), 0.8–1.0(16H,m), 2.15–3.1(4H,m), 4.0–4.2(2H,m), 4.3–4.55(2H,m), 4.95–5.4(3H,m), 5.65–5.9(1H,m), 7.93(1H,m); m/e 439 (M+H)+.

(iii) Sodium methoxide solution (30% w/w in methanol; 15.5 ml) was added to a solution of compound J (34.4 g) in methanol (150 ml) at 5° C. and the mixture stirred for 15 minutes. Saturated aqueous ammonium chloride solution (200 ml) was then added and the mixture extracted three times with ethyl acetate. The combined extracts were washed with brine, concentrated, and the residue was purified by column chromatography, eluting first with hexane, and then increasing gradually to 50% v/v ethyl acetate/hexane, to give methyl (2S)-2-[(1S)-1-hydroxy-1-(5-[2-tert-butyldimethylsilyl]-thiazolyl)methyl]pent-4-enoate (K) (65% yield) as an oil; NMR: 0.3(6H,s), 0.9(9H,s), 2.2–2.55(2H,m), 2.8–2.9(1H,m), 3.1–3.4(OH,m), 3.56 and 3.65(isomers,3H,2s), 4.9–5.3(3H,m), 5.7(1H,m), 7.86 and 7.87(isomers,1H,2s); $^{20}[\alpha]_D$ +39.3° (c 1.0, ethanol).

EXAMPLES 3 and 4

Using an analogous procedure to that described in Example 1, but starting from the appropriate ester, the following acids were obtained:

(Example 3): 4(Z)-6-[(2,4,5-cis)-2-(4-cyanophenyl)-4-(5-thiazolyl)-1,3,-dioxan-5-yl]hexenoic acid as an oil, in 55% yield; NMR: 1.7–2.0(2H,m), 2.2–2.5(4H,m), 2.55–2.75(1H,m), 3.0–4.5(1H, broad s), 4.05–4.35(2H,m), 5.2–5.6(3H,m), 5.77(1H,s), 7.6–7.9(5H,m), 8.80(1H,s); microanalysis found: C, 61.8; H, 5.4; N, 6.9%; C$_{20}$H$_{20}$N$_2$O$_4$S.1/5H$_2$O requires: C, 61.9; H, 5.3; N, 7.2%; m/e 385 (M+H)+.

The starting ester was obtained using an analogous procedure to that described in Example 1, part (vii), but using 4-cyanobenzaldehyde instead of 2-(4-methyl-2-nitrophenoxy)-2-methylpropanal. Methyl 4(Z)-6-[(2,4,5-cis)-2-(4-cyanophenyl)-4-(4-thiazolyl)-1,3-dioxan-5-yl]hexenoate was thus obtained as an oil, in 70% yield; NMR: 1.7–2.0(2H,m), 2.3–2.35(4H,m), 2.6(1H,m), 3.63(3H,s), 4.05–4.35(2H,m), 5.24–5.6(3H,m), 5.77(1H,s), 7.6–7.8(5H,m), 8.79(1H,s).

(Example 4): 4(Z)-6-[(2,4,5-cis)-2-(4-trifluoromethylphenyl)-4-(5-thiazolyl)-1,3,-dioxan-5-yl[hexenoic acid as an oil, in 53% yield; NMR: 1.7–2.0(2H,m), 2.2–2.45(4H,m), 2.55–2.75(1H,m), 4.05–4.35(2H,m), 5.25–5.6(3H,m), 5.78(1H,s), 7.68(4H,s), 7.80(1H,s), 8.80(1H,s); m/e 428 (M+H)$^{30}$.

The starting ester was obtained using an analogous procedure to that described in Example 1, part (vii), but using 4-trifluoromethylbenzaldehyde instead of 2-(4-methyl-2-nitrophenoxy)-2-methylpropanal. Methyl 4(Z)-6-[(2,4,5-cis)-2-(4-trifluoromethylphenyl)4-(4-thiazolyl)-1,3-dioxan-5-yl[hexenoate was thus obtained as an oil, in 45% yield; NMR: 1.7–2.0(2H,m), 2.25–2.45(4H,m), 2.65(1H,m), 3.63(3H,s), 4.04–4.35(2H,m), 5.24–5.6(3H,m), 5.77(1H,s), 7.6–7.85(5H,m), 8.79(1H,s).

EXAMPLES 5–7

Using an analogous procedure to that of Example 2, but starting from the appropriate ester, the following acids of the formula I were obtained:

(Example 5): 4(Z)-6-[(2S,4S,5R)-2-(1-(4-chloro-2-cyanophenoxy)-1-methylethyl-4-(5-thiazolyl)-1,3-dioxan-5-yl]hexenoic acid, as an oil; NMR:1.47(3H,s), 1.49(3H,s), 1.65–1.85(2H,m), 2.20–2.60(5H,m), 3.95–4.2(2H,m), 4.96(1H,s), 5.25–5.54(3H,m), 7.18(1H,m), 7.44(2H,m), 7.69(1H,s), 8.78(1H,s); m/e 477 (M+H)+.

(Example 6): 4(Z)-6-[(2S,4S,5R)-2-(4-cyanophenyl)-4-(5-thiazolyl)-1,3-dioxan-5-yl]hexenoic acid as an oil; NMR and mass spectral data was similar to that of the product of Example 3.

(Example 7): 4(Z)-6-[(2S,4S,5R)-2-(1-(2-cyano-4-ethylphenoxy)-1-methylethyl)-4-(5-thiazolyl)-1,3-dioxan-5-yl]hexenoic acid as a solid, m.p. 116°–119° C.; NMR: 1.21(3H,t), 1.45(3H,s), 1.48(3H,s), 1.65–1.86(2H,m), 2.25–2.40(4H,m), 2.42–2.70(3H,m), 3.95–4.20(2H,m), 4.97(1H,s), 5.25–5.53(3H,s), 7.11(1H,m), 7.28(1H,m), 7.32(1H,m), 7.66(1H,s), 8.75(1H,s); m/e 471(M+H)+; microanalysis, found: C,63.6; H,6.6; N,5.8%; C$_{25}$H$_{30}$N$_2$O$_5$S requires: C,63.8; H,6.4; n,6.0%.

The starting esters used in Examples 5–7 were obtained using an analogous procedure to that described in Example 2 for the preparation of compound H, but using the appropriate aldehyde in instead of 2-(4-methyl-2-nitrophenoxy)-2-methylpropanal, as follows: (5): methyl 4(Z)-6-[(2S,4S,5R)-2-(1-(4-chloro-2-cyanophenoxy)-1-methylethyl-4-(5-thiazolyl)-1,3-dioxan-5-yl]hexenoate was obtained as an oil, in 43% yield; NMR: 1.47(3H,s), 1.49(3H,s), 1.65–1.90(2H,m), 2.20–2.60(5H,m), 3.65(3H,s), 3.95–4.20(2H,m), 4.95(1H,s), 5.20–5.55(3H,m), 7.18(1H,m), 7.44(2H,m), 7.69(1H,s), 8.78(1H,s).

(6): methyl 4(Z)-6-[(2S,4S,5R)-2-(4-cyanophenyl)-4-(5-thiazolyl)-1,3-dioxan-5-yl]hexenoate was obtained as an oil, in 46% yield; NMR spectral data was similar to that of the starting ester used in Example 3.

(7): methyl 4(Z)-6-[(2S,4S,5R)-2-(1-(2-cyano-4-ethylphenoxy)-1-methylethyl-4-(5-thiazolyl)-1,3-dioxan-5-yl]hexenoate was obtained as an oil, in 55% yield; NMR: 1.45(3H,s), 1.48(3H,s), 1.6–1.85(2H,m), 2.20–2.60(5H,m), 3.65(3H,s), 3.95–4.20(2H,m), 4.99(1H,s), 5.20–5.58(3H,m), 7.11(1H,m), 7.29(2H,m), 7.64(1H,s), 8.72(1H,s).

2-(4-Chloro-2-cyanophenoxy)-2-methylpropanal was obtained as follows:

(i) Pyridine (20 ml) was added to a stirred suspension of 5-chloro-2-hydroxybenzaldehyde (5.0 g) and hydroxylamine hydrochloride (2.77 g) in ethanol (20 ml) and stirring was continued for 18 hours. The mixture was then added to water (150 ml) and extracted with ether (3×50 ml). The combined extracts were washed with water (2×50 ml), dried (MgSO4) and concentrated to give a yellow oil which slowly crystallised on standing. The solid was collected by filtration and washed with hexane to give 5-chloro-2-hydroxybenzaldoxime (4.25 g) as white crystals, m.p. 125°–126° C.; NMR: 6.91(1H,d,J=8 Hz), 7.15(1H,d,J=2.5 Hz), 7.22(1H,dd,J=8,2.5 Hz); 7.55(1H,b), 8.16(1H,s), 9.26(1H,b).

(ii) A solution of 5-chloro-2-hydroxybenzaldoxime (4.2 g) in acetic anhydride (15 ml) was heated for 4 hours at reflux, then allowed to stand for 16 hours at ambient temperature. The mixture was added to a vigorously stirred ice-water mixture and after one hour the resulting solid was collected by filtration. 2M Sodium hydroxide solution (120 ml) was added to a stirred solution of this solid in methanol (50 ml) and the mixture stirred for 20 minutes. The pH of the mixture was then adjusted to 4.0 with 2M hydrochloric acid solution. The mixture was cooled to 4° C. and the white precipitate collected by filtration to give 4-chloro-2-cyanophenol (2.6 g), m.p. 166°–168° C.; NMR (CDCl3/d6-DMSO): 6.69(1H,d,J=8 Hz), 7.04(1H,dd,J=8,2.5 Hz), 7.11(1H,d,J=2.5 Hz), 10.33(1H,s).

(iii) Anhydrous potassium carbonate (2.76 g) was added to a stirred solution of 4-chloro-2-cyanophenol (1.53 g) and 2-bromo-2-methyl propanal (2.26 g) in THF (50 ml) and the mixture heated at reflux for 5 hours. The mixture was then cooled to 4° C., the suspended solid removed by filtration and the filtrate evaporated to give a yellow oil which crystallised on standing. The solid was triturated with hexane and collected by filtration to give 2-(4-chloro-2-cyanophenoxy)-2-methylpropanal (2.11 g), m.p. 85°–88° C.; NMR: 1.52(6H,s), 6.79(1H,d,J=8 Hz), 7.42(1H,dd,J=8,2.5 Hz), 7.57(1H,d,J=2.5 Hz), 9.80(1H,s).

2-(2-Cyano-4-ethylphenoxy)-2-methylpropanal was obtained as follows:

(i) A solution of 4-ethylphenol (2.44 g) in dichloromethane (10 ml), was added to a stirred, ice-cooled, solution of 1M boron trichloride in dichloromethane (24 ml) under argon, followed by methylthiocyanate (1.64 ml), and then anhydrous aluminium chloride (2.66 g). The mixture was stirred for 1 hour at 4° C., then heated at reflux (bath temperature 60° C.) for 4 hours and finally stirred for 16 hours at ambient temperature. The mixture was added cautiously to a stirred, ice-cooled, 4M sodium hydroxide solution and the resultant mixture heated at 70° C. for 30 minutes then cooled. The aqueous phase was separated, washed with dichloromethane (2×25 ml), then acidified to pH 2 with 6M hydrochloric acid and extracted with ethyl acetate (3×75 ml). The combined organic extracts were washed with saturated brine (3×50 ml), dried (MgSO4) and the solvent removed in vacuo to give a brown solid. Purification by flash chromatography, eluting with 20% v/v ethyl acetate in hexane, followed by recrystalisation from hexane gave 2-cyano-4-ethylphenol (A) (2.56 g), m.p. 95°–98° C.; NMR: 1.21 (3H, t, J=7 Hz), 2.59 (2H, q, J=7 Hz), 5.70 (1H, b), 6.90 (1H, m), 7.29 (2H, m).

(ii) 2-Cyano-4-ethylphenol (1.47 g) was added portionwise to a stirred, ice-cooled suspension of sodium hydride (60% w/w dispersion in mineral oil, 420 mg) in DMPU (10 ml) under argon. Stirring was continued for 1 hour at ambient temperature, the mixture cooled to 4° C. and 2-bromo-2-methylpropanal (2.26 g) in DMPU (2 ml) added. Stirring was continued for 18 hours at ambient temperature. Water (50 ml) was added and the resulting mixture extracted with ether (3×50 ml). The combined extracts were washed with water (2×30 ml) and saturated brine (2×30 ml), then dried (MgSO4). Evaporation of the solvent and purification of the residual oil by flash chromatography, eluting with 20% v/v ethyl acetate in hexane, gave 2-(2-cyano-4-ethylphenoxy)-2-methylpropanal (2.04 g), as a colourless oil; NMR: 1.21 (3H, t, J=7 Hz), 1.51 (6H, s), 2.61 (2H, q, J=7 Hz), 6.76(1H, d, J=7 Hz), 7.28 (1H, dd, J=7,2 Hz), 7.41 (1H, d, J=2 Hz), 9.85 (1H, s).

EXAMPLES 8–11

Using a procedure analagous to that of Example 2, but starting from the appropriate ester, the following acids of formula I were obtained:

(Example 8): 4(Z)-6-[(2S,4S,5R)-2-(1-(4-(1-methylethyl)-2-cyanophenoxy)-1-methylethyl-4-(5-thiazolyl)-1,3-dioxan-5-yl]hexenoic acid as a solid, m.p. 107°–111° C.; NMR: 1.20(3H,s), 1.22(3H,s), 1.45(3H,s), 1.48(3H,s), 1.65–1.86(2H,m), 2.22–2.60(5H,m), 2.88(1H,m), 3.95–4.20(2H,m), 4.98(1H,sd), 5.22–5.55(3H,m), 7.10(1H,m), 7.32(1H,m), 7.63(1H,s), 8.74(1H,s); m/e 485(M+H)+.

(Example 9): 4(Z)-6-[(2S,4S,5R)-2-(1-(4-acetyl-2-nitrophenoxy)-1-methylethyl-4-(5-thiazolyl)-1,3-dioxan-5-yl]hexenoic acid as an oil; NMR: 1.48(3H,s), 1.50(3H,s), 1.6–1.9(2H,m), 2.15–2.55(3H,m), 2.6(3H,s), 2.0–3.4(1H,br.s), 3.8–4.2(2H,m), 4.82(1H,s), 5.2–5.52(3H,m), 7.43(1H,d,J=3 Hz), 7.69(1H,s), 8.06(1H,m), 8.23(1H,m), 8.78(1H,s); m/e 505(M+H)+.

(Example 10): 4(Z)-6-[(2S,4S,5R)-2-(1-(2-trifluoromethylphenoxy)-1-methylethyl-4-(5-thiazolyl)-1,3-dioxan-5-yl]hexenoic acid as an oil; NMR: 1.45(3H,s), 1.51(3H,s), 1.7–1.8(1H,m), 1.81–1.94(1H,m), 2.3–2.4(4H,m), 2.5–2.64(1H,m), 3.98(1H,m), 4.21(1H,m), 4.89(1H,s), 5.28–5.54(3H,m), 7.08(1H,m), 7.35–7.45(2H,m), 7.54(1H,m), 7.75(1H,s), 8.79(1H,s); m/e 486(M+H)+.

(Example 11): 4(Z)-6-[(2S,4S,5R)-2-(1-(4-methylthio-2-nitrophenoxy)-1-methylethyl-4-(5-thiazolyl)-1,3-dioxan-5-yl]hexenoic acid as a solid, m.p. 122°–123° C.;

NMR: 1.41(s,6H), 1.62–1.83(2H,m), 2.20–2.53(6H,m), 3.84–3.95(1H,m), 4.07–4.14(1H,m), 4.79(1H,m), 5.2–5.52(3H,m), 7.19(1H,m), 7.32(1H,m), 7.52(1H,m), 7.69(1H,s), 8.77(1H,s); m/e 509(M+H)+.

The starting esters used in Examples 8–11 were prepared by a procedure analogous to that described in Example 2 for the preparation of compound H, but using the appropriate aldehyde instead of 2-(4-methyl-2-nitrophenoxy)-2-methylpropanal:

(8): methyl 4(Z)-6-[(2S,4S,5R)-2-(1-(4-(1-methylethyl)-2-cyanophenoxy)-1-methylethyl-4-(5-thiazolyl)-1,3-dioxan-5-yl]hexenoate: NMR: 1.20(3H,s), 1.24(3H,s), 1.46(3H,s), 1.50(3H,s), 1.6–1.9(2H,m), 2.2–2.6(5H,m), 2.76–3.0(1H,m), 3.65(3H,s), 3.94–4.24(2H,m), 4.98(1H,s), 5.2–5.6(3H,m), 7.1(1H,m), 7.28–7.39(2H,m), 7.63(1H,s), 8.72(1H,s).

(9): methyl 4(Z)-6-[(2S,4S,5R)-2-(1-(4-acetyl-2-nitrophenoxy)-1-methylethyl-4-(5-thiazolyl)-1,3-dioxan-5-yl]hexenoate: NMR: 1.51(3H,s), 1.59(3H,s), 1.6–1.9(2H,m), 2.2–2.6(5H,m), 3.63(3H,m), 4.91(1H,m), 4.12(1H,m), 4.83(1H,s), 5.19–5.52(3H,m), 7.43(1H,d,J=8.3 Hz), 7.69(1H,s), 8.06(1H,dd,J=8.3,<1 Hz), 8.26(1H,d,J=>1 Hz), 8.73(1H,s).

(10): methyl 4(Z)-6-[(2S,4S,5R)-2-(1-(2-trifluoromethylphenoxy)-1-methylethyl-4-(5-thiazolyl)-1,3-dioxan-5-yl]hexenoate: NMR: 1.52(3H,s), 1.55(3H,s), 1.67–1.92(2H,m), 2.25–2.65(5H,m), 3.65(3H,s), 3.97(1H,m), 4.21(1H,m), 4.89(1H,s), 5.22–5.55(3H,m), 7.07(1H,m), 7.32–7.47(2H,m), 7.54(1H,m), 7.73(1H,s), 8.77(1H,s).

(11): methyl 4(Z)-6-[(2S,4S,5R)-2-(1-(4-methylthio-2-nitrophenoxy)-1-methylethyl-4-(5-thiazolyl)-1,3-dioxan-5-yl]hexenoate: NMR: 1.41(6H,s), 1.61–1.86(2H,m), 2.18–2.54(8H,m), 3.63(3H,s), 3.90(1H,m,), 4.10(1H,m), 4.79(1H,s), 5.20–5.52(3H,m), 7.20–7.46(3H,m), 7.52(1H,m), 7.68(1H,s), 8.74(1H,s).

The starting aldehydes were prepared by a procedure analagous to that described in Example 7 for the preparation of 2-(2-cyano-4-ethylphenoxy)-2-methylpropanal, but using the appropriate phenol instead of 2-cyano-4-ethylphenol, as follows:

(1) 2-(2-cyano-4-(1-methylethyl)phenoxy)-2-methylpropanal as an oil; NMR: 1.22(3H,s), 1.24(3H,s), 1.52(6H,s), 2.88(1H,m), 6.76(1H,d J=7 Hz), 7.30(1H,dd J=7.2 Hz), 7.44(1H,d, J=2 Hz), 9.83(1H,s).

(2) 2-(4-acetyl-2-nitrophenoxy)-2-methylpropanal as an oil; NMR: 1.58(6H,s), 2.60(3H,s), 6.96(1H,d,J=8 Hz), 8.05(1H,dd,J=8 Hz), 8.36(1H,d,J=3 Hz), 9.81(1H,s).

(3) 2-(2-trifluoromethylphenoxy)-2-methylpropanal as an oil; NMR: 1.49(6H,s), 6.77–7.11(2H,m), 7.26–7.62 (2H,m), 9.86(1H,s).

(4) 2-(2-nitro-4-(methylthio)phenoxy)-2-methylpropanal as an oil; NMR: 1.5(6H,s), 2.5(3H,s), 6.9(1H,d,J=8 Hz), 7.51(1H,dd,J=8 Hz), 7.95(1H,d,J=3 Hz), 10.47(1H,s).

The 2-cyano-4-(1-methylethyl)phenol used to prepare 2-(2-cyano-4-(1-methylethyl)phenoxy-2-methylpropanal was obtained as a crystalline solid; m.p. 93°–95° C.; NMR: 1.22(3H,s), 1.24(3H,s), 2.87(1H,m), 5.87(1H,b), 6.91(1H,m), 7.33(2H,m).

2-Nitro-4-(methylthio)phenol was prepared as follows:

To a solution of 4-(methylthio)phenol(5.0 g) in methylene chloride (100 mls) was added 30% nitric acid absorbed on silica (9.29 g) and the mixture stirred at room temperature for 3 hrs. The mixture was filtered and washed with methylene chloride. The solvent was evaporated and the residue was purified by flash chromatography eluting with ethyl acetate and hexane (15:85 v/v) to give 2-nitro-4-(methylthio)phenol as an orange solid (2.22 g); NMR (200 MHz, CDCl3): 2.50(3H,s), 7.10(1H,d,J=8 Hz), 7.51(1H,dd,J=8 Hz), 7.95(1H,d,J=3 Hz).

EXAMPLE 12

Using a similar procedure to that described in Example 1, but starting from methyl 4(Z)-6-[(2S,4S,5R)-2-(1-(4-methyl-2-nitrophenoxy)-1-methylethyl-4-(5-(1-hexyl)imidazolyl)-1,3-dioxan-5-yl]hexenoate there was obtained 4(Z)-6-[(2S,4S,5R)-2-(1-(4-methyl-2-nitrophenoxy)-1-methylethyl-4-(5-(1-hexyl)imidazolyl)-1,3-dioxan-5-yl]hexenoic acid as an oil; NMR: 0.8–1.0(3H,m), 1.15–1.45(12H,m), 1.65–1.9(4H,m), 2.0–2.6(8H,m), 3.85–4.2(4H,m), 4.79(1H,s), 5.0(1H,s), 5.25–5.55(2H,m), 6.98(1H,s), 7.1–5(4H,m); MS m/e 544(M+H)+.

The starting material was prepared as follows:

(i) Imidazole-5-carboxylic acid (10.0 g, 89 mmol) was dissolved in methanol (185 ml) and concentrated sulphuric acid (10 ml) was added dropwise. The mixture was heated under reflux for two days. After cooling in ice and neutralising with dilute sodium hydroxide solution the solvents were removed by evaporation. The white solid produced was suspended in methanol (70 ml) and hexyl iodide (26.3 ml, 178 mmol) in methanol (30 ml) was added. After heating under reflux overnight, the mixture was cooled and filtered through a pad of diatomaceous earth, washing well with methanol. The filtrate was concentrated and the residue purified by column chromatography, eluting with 1.5% methanol/dichloromethane (v/v), to give methyl 1-hexylimidazole-5-carboxylate (1.4 g; 7.5% yield), as an oil; NMR: 0.82–0.97(3H,m), 1.2–1.9(8H,m), 3.86(3H,s), 4.29(2H,t,J=7.5 Hz), 7.58(1H,s), 7.72(1H,s).

(ii) A solution of the product of step (i) (420 mg, 2 mmol) in THF (15 ml) was added to a suspension of lithium aluminium hydride (380 mg, 10 mmol) in THF (15 ml) with stirring at 0° C. under argon. After 1 hour a saturated aqueous solution of sodium carbonate (1 ml) was added dropwise and the mixture was stirred for a further 15 minutes before being filtered through a pad of diatomaceous earth, washing well with ethyl acetate. The filtrate was evaporated to give 1-hexyl-5-hydroxymethylimidazole (349 mg, 96% yield) as a solid; NMR: 0.8–0.95(3H,m), 1.2–1.45(6H,m), 1.7–1.9(2H,m), 3.99(2H,t,J=7.5 Hz), 4.62(2H,s), 6.93(1H,s), 7.46(1H,s).

(iii) A solution of dimethyl sulphoxide (0.49 ml, 7.74 mmol) in dichloromethane (2.5 ml) was added dropwise to a solution of oxalyl chloride (0.3 ml, 3.78 mmol) in dichloromethane (15 ml) at −78° C. with stirring under argon. After effervescence had ceased (15 min), a solution of the product of step (ii) (313 mg, 1.72 mmol) in dichloromethane (7.5 ml) was added dropwise. The solution was stirred for 15 minutes before triethylamine (2.3 ml, 19 mmol) was added slowly. After a further 15 minutes the solution was allowed to warm to room temperature, stirred for 30 minutes and then quenched by the addition of a saturated aqueous solution of sodium bicarbonate (10 ml). The mixture was extracted with ethyl acetate (3×10 ml). The extracts were washed with brine (1×10 ml), dried (MgSO4) and concentrated. The residue was purified by column chromatography, eluting with 10% methanol/dichloromethane (v/v), to give 1-hexyl-imidazole-5-carboxaldehyde (280 mg, 90% yield) as an oil; NMR: 0.8–0.95(3H,m), 1.2–1.4(6H,m), 1.68–1.9(2H,m), 4.29(2H,t,J=7. Hz), 7.65(1H,s), 7.80(1H,s), 9.74(1H,s).

(iv) 4(Z)-octenedioic acid monomethyl ester (prepared according to the method described in H. Klunenberg & H. J. Schafer, Agnew. Chem. Int. Ed. Engl., (1978), 17, 47) (11.6 g, 62.4 mmol) was dissolved in THF (200 ml) and oxalyl chloride (10.88 ml, 124.7 mmol) was added slowly with stirring under argon at 0° C., followed by 1 drop of dimethylformamide. The mixture was allowed to warm to room temperature and stirred for three hours before the solvents were removed by evaporation. Meanwhile, 4S-(−)-4-isopropyl-2-oxazolidinone (12.07 g, 93.6 mmol) was dissolved in THF (400 ml) and the solution cooled to −78° C. n-Butyl lithium (1.6M solution in hexanes, 60 ml, 93.6 mmol) was added dropwise. A thick white suspension formed. After 30 minutes a solution of the freshly-formed acid chloride in THF (200 ml) was added and the mixture was allowed to warm to room temperature and stirred overnight, whereupon a clear solution was formed. A saturated aqueous solution of ammonium chloride (300 ml) was added, and the mixture was extracted with ethyl acetate (3×250 ml). The extracts were washed with brine (150 ml), dried (MgSO4), filtered and concentrated. The residue was purified by column chromatography, eluting with 20% ethyl acetate/hexane (v/v), to give methyl (Z)-8-[(S)-4-isopropyl-2-oxo-1,3-oxazinan-3-yl]-8-oxo-oct-4-enoate (9.35 g, 51% yield) as an oil; NMR: 0.85–0.97(6H,m), 2.3–2.5(7H,m), 2.84–3.12(2H,m), 3.68(3H,s), 4.2–4.5(m,3H), 5.15–5.52(m,2H); MS m/e 298(M+H)+.

(v) A 1M solution of dibutylboron triflate in dichloromethane (1.56 ml) was added to a solution of the product of step (iv) (422 mg, 1.42 mmol) in dry dichloromethane (9 ml) at 5° C. under argon, followed by diisopropylethylamine (0.295 ml, 1.7 mmol). The reaction mixture was stirred at 5° C. for 30 minutes and then cooled to −78° C. A solution of the product of step (iii) (280 mg, 1.56 mmol) in dichloromethane (2 ml) was added dropwise. The mixture was stirred at −78° C. for 30 minutes before being allowed to warm to room temperature. The reaction was quenched by the addition of pH7.2 phosphate buffer solution (1.36 ml) followed by hydrogen peroxide (0.4 ml, 30% w/v aqueous solution). The mixture was stirred for 30 minutes and then poured into water and extracted three times with dichloromethane. The combined extracts were dried (MgSO4), filtered, and evaporated. The residue was purified by column chromatography, eluting with ethyl acetate, to give methyl (7S,4Z)-7-[(S)-(1-hexylimidazol-5-yl)hydroxymethyl]-8-[(S)-4-isopropyl-2-oxo-1,3-oxazinan-3-yl]-8-oxo-oct-4-enoate (450 mg, 66% yield) as an oil; NMR 0.8–0.95(9H,m), 1.25–1.4(6H,m), 1.7–1.9(2H,m), 2.1–2.9(8H,m), 3.68(3H,s), 3.85–4.22(4H,m), 4.6–4.72(1H,m), 4.88(1H,m), 5.36–5.6(2H,m), 6.93(1H,s), 7.54(1H,s).

(vi) Sodium borohydride (4×36 mg, 3.8 mmol) was added in batches at 30 minute intervals to a solution of the product of step (v) in methanol (4 ml) at 0° C. with stirring under argon. After stirring for a further 30 minutes, a saturated aqueous solution of ammonium chloride (5 ml) was added slowly. The mixture was extracted with ethyl acetate (3×10 ml) and the combined extracts dried (MgSO4), filtered and concentrated by evaporation. The residue was purified by column chromatography, eluting with 10% methanol/dichloromethane (v/v), to give methyl (7S,4Z)-7-[(S)-(1-hexylimidazol-5-yl)hydroxymethyl]-8-hydroxyoct-4-enoate (200 mg, 60% yield) as an oil; NMR: 0.8–1.0(3H,m), 1.2–1.4(6H,m), 1.7–1.87(2H,m), 1.9–2.1(1H,m), 2.15–2.63(6H,m), 2.8–3.1(2H,br s), 3.57–3.83(5H,m), 3.83–4.05(2H,m), 4.97(1H,d,J=5 Hz), 5.3–5.5(2H,m), 6.93(1H,s), 7.47(1H,s).

(vii) p-Toluenesulphonic acid monohydrate (74 mg, 0.37 mmol) was added to a solution of the product of step (vi) (130 mg, 0.37 mmol), 2-(4-methyl-2-nitrophenoxy)-2-methylpropanal (prepared as in European Patent Application, Publication No. 365328) (109 mg, 0.56 mmol), and trimethylorthoformate (83 mg, 0.78 mmol) in acetonitrile (5 ml), and the mixture was stirred at reflux for 1 hour. The condenser was removed and the mixture heated at 110° C. for 3 hours. The mixture was cooled and diluted with ethyl acetate (5 ml). Saturated aqueous sodium bicarbonate solution (5 ml) was added, and the layers separated. The aqueous phase was extracted three times with ethyl acetate. The combined organic phases were dried (MgSO4) and concentrated by evaporation to give an oil which was purified by column chromatography, eluting first with 25% ethyl acetate/hexane (v/v) and then 5% methanol/dichloromethane (v/v), to give methyl 4(Z)-6-[(2S,4S,5R)-2-(1-(4-methyl-2-nitrophenoxy)-1-methylethyl-4-(5-(1-hexyl)imidazolyl)-1,3-dioxan-5-yl]hexenoate (94 mg, 46% yield), as an oil; NMR: 0.8–1.0(3H,m), 1.2–1.45(12H,m), 1.65–1.9(4H,m), 2.1–2.65(8H,m), 3.65(3H,s), 3.85–4.15(4H,m), 4.80(1H,s), 5.02(1H,s), 5.25–5.55(2H,m), 6.89(1H,s), 7.05–7.55(4H,m).

EXAMPLE 13

Using a similar procedure to that described in Example 1, but starting from methyl 4(Z)-6-[(2S,4S,5R)-2-(1-(4-methyl-2-nitrophenoxy)-1-methylethyl-4-(5-(1-methylimidazolyl)-1,3-dioxan-5-yl]hexenoate, there was obtained 4(Z)-6-[(2S,4S,5R)-2-(1-(4-methyl-2-nitrophenoxy)-1-methylethyl-4-(5-(1-methylimidazolyl)-1,3-dioxan-5-yl) hexenoic acid as a foam; NMR: 1.45(3H,s) 1.48(3H,s), 1.6–2.4(10H,m), 3.65(3H,s), 3.85–4.15(2H,m), 4.75(1H,s), 5.0(1H,s), 5.3–5.5(2H,m), 6.95–7.85(5H,m).

The starting material was prepared in a similar manner to that used in Example 12

(i) Using a procedure analogous to that described in Example 12, step (v), but using 1-methyl imidazole-5-carboxaldehyde (preparation described in P. K. Martin JOC (1968) 33,3758 and also in R. G. Jones JACS (1949) 71,2444) there was obtained methyl 4(Z)-7(S)-[(1S)-1-hydroxy-1-[5-[1-methyl]imidazolyl]methyl-8-[(4S)-isopropyl-2-oxo-1,3-oxazinan-3-yl]-8-oxo-oct-4-enoate as a foam in 59% yield; NMR: 0.8–0.9(6H,m), 2.15–2.4 (4H,m), 2.6–2.95(2H,m), 3.6–3.75(7H,m), 4.1–4.25(3H,m), 4.55–4.65(1H,m), 4.9–4.95(1H,m), 5.4–5.6(2H,m), 6.83(1H,s), 7.40(1H,s).

(ii) Using an analogous procedure to that described in Example 12, step (vi) there was obtained methyl 4(Z)-(7R,8S)-8-hydroxy-7-hydroxymethyl-8-(5-(1-methylimidazolyl)-4-octenoate as an oil in 48% yield; NMR: 1.95–2.1(1H,m), 2.2–2.6(6H,m), 3.55–3.8(10H,m), 4.95(1H,d,J=6 Hz), 5.35–5.5(2H,m), 6.88(1H,s), 7.37(1H,s).

(iii) Using an analogous procedure to that described in Example 12, step (vii) there was obtained methyl 4(Z)-6-[(2S,4S,5R)-2-(1-(4-methyl-2-nitrophenoxy)-1-methylethyl)-4-(5(1-methylimidazolyl)-1,3-dioxan-5-yl]hexenoate as an oil in 36% yield; NMR: 1.38(3H,s), 1.40(3H,s), 1.6–1.75(1H,m), 2.1–2.4(8H,m), 2.5–2.7(1H,m), 3.63(3H,s), 3.65(3H,s), 3.85–4.15(2H,m), 4.81(1H,s), 5.04(1H,d,J=3 Hz), 5.25–5.55(2H,m), 6.9–7.5(5H,m).
CHEMICAL FORMULAE
(in description)
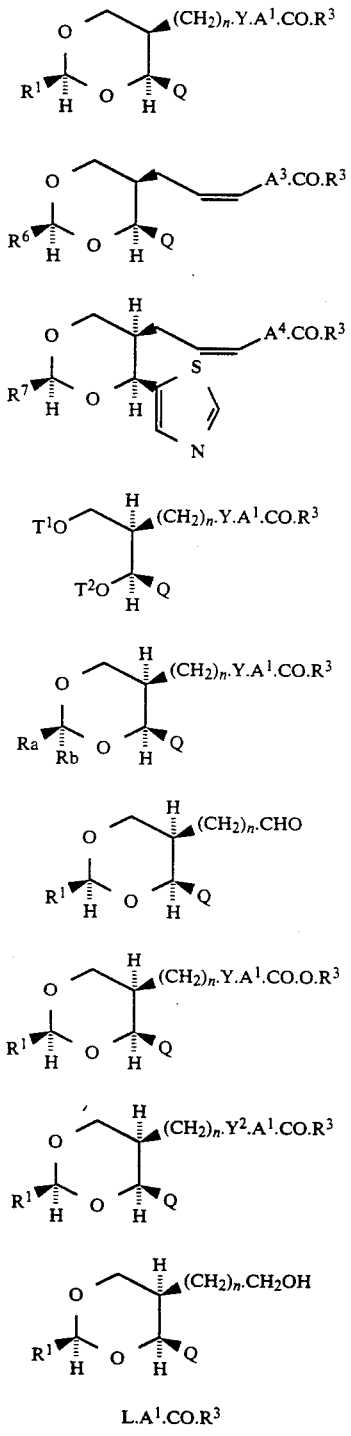
L.A¹.CO.R³
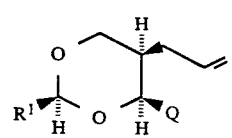
-continued
CHEMICAL FORMULAE
(in description)
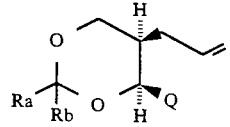  XII
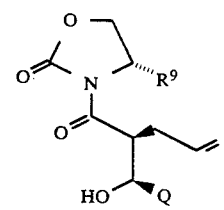  XIII
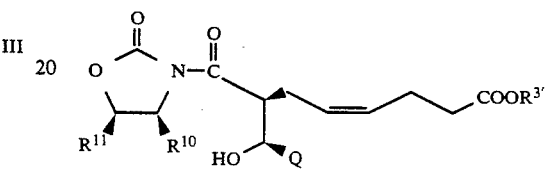  XIV
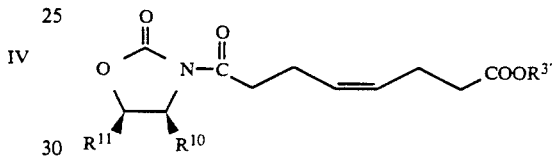  XV
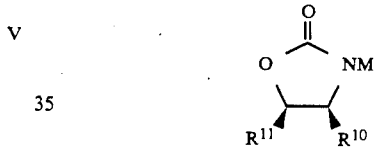  XVI
  XVII
SCHEME 1
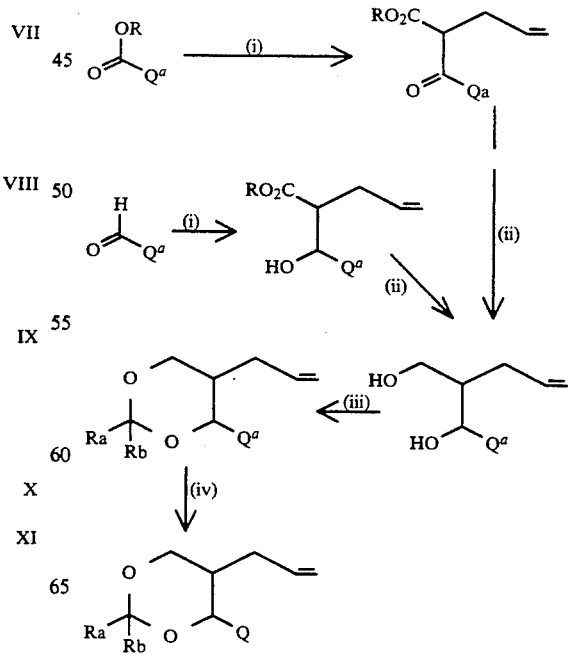

SCHEME 2

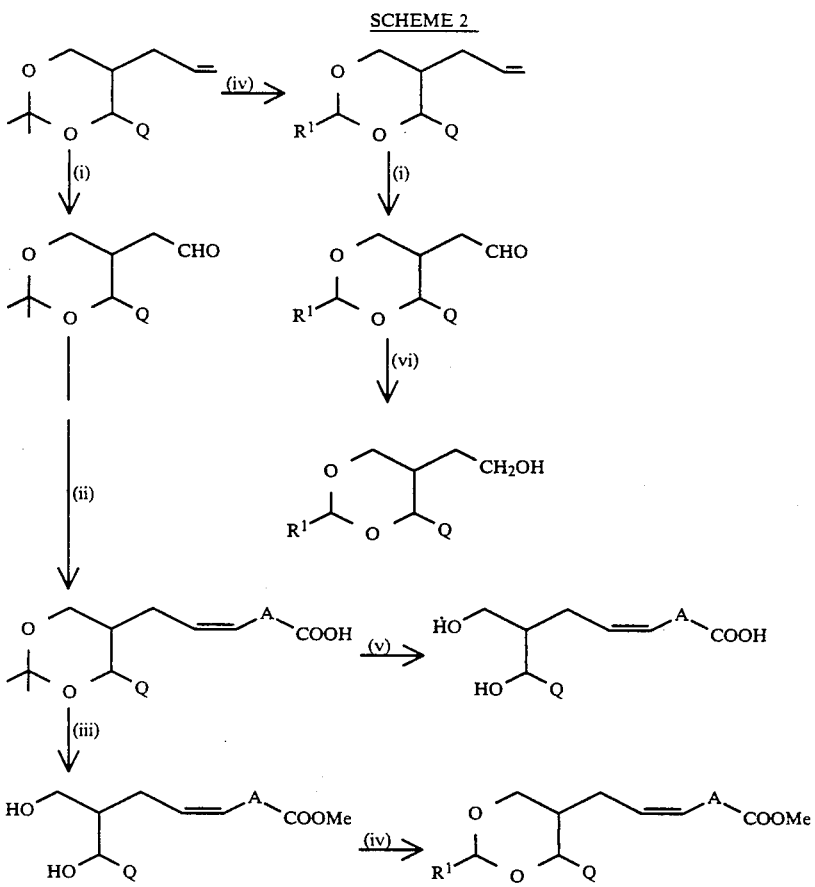

Reagents:
(i) O$_3$, methanol, −78° C.; then (CH$_3$)$_2$S
(ii) Br$^-$ (Ph)$_3$P$^+$.CH$_2$.A$^1$.CO$_2$H, potassium tert-butoxide, THF
(iii) HCl, methanol
(iv) R$^1$.CHO, TsOH, CH$_3$CN
(v) HCl, H$_2$O, THF
(vi) NaBH$_4$, ethanol -continued
SCHEME 1

Reagents:
(i) CH$_2$=CH—CH$_2$.CH$_2$.CO.O.R, [(CH$_3$)$_3$CH]$_2$NLi, THF, −78° C.
(ii) NaBH$_4$, ethanol
(iii) TsOH, Ra.Rb.CO or Ra Rb.C(OMe)$_2$
(iv) optional deprotection Note: R = (1–4C)alkyl, such as methyl (Me) or ethyl(Et);
Ts = p-toluenesulphonyl
Q$^a$ = Q or Q bearing a protecting group

SCHEME 3

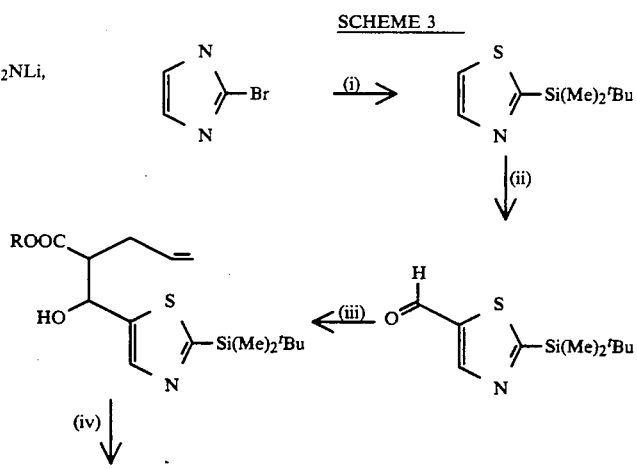

SCHEME 3

-continued

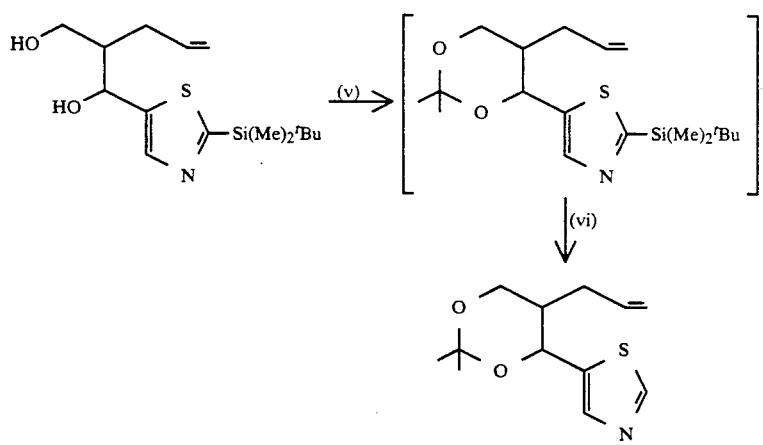

Reagents:
(i) tert-butyldimethylsilyl chloride/BuLi/THF/−78° C.
(ii) BuLi, THF, −78° C.; then (CH$_3$)$_2$.NCHO
(iii) CH$_2$=CH.CH$_2$.CH$_2$.CO.O.R, [(CH$_3$)$_2$CH]$_2$NLi, THF, −78° C.
(iv) LiAlH$_4$, THF
(v) TsOH, Ra.Rb.CO or Ra.Rb.C(OCH$_3$)$_2$
(vi) Tetrabutylammonium fluoride, THF

SCHEME 4

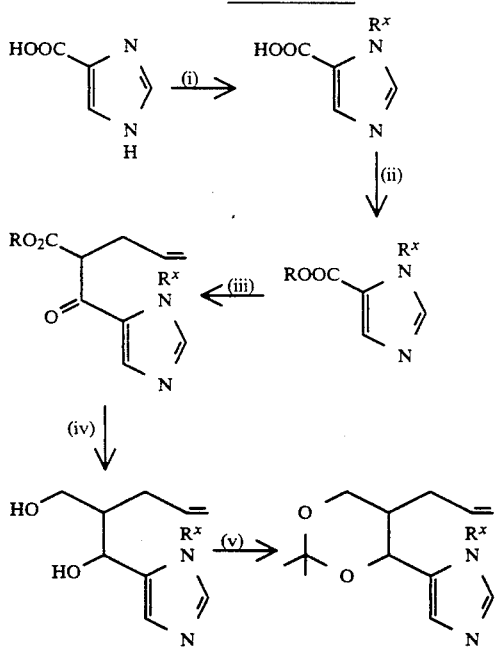

Reagents:
(i) R$^x$.I, ethanol
(ii) ROH, HCl
(iii) CH$_2$=CH—CH$_2$.CH$_2$.CO.O.R, [(CH$_3$)$_2$CH]$_2$NLi, THF, −78° C.
(iv) NaBH$_4$, ROH
(v) TsOH, Ra.Rb.CO or Ra.Rb.C(OCH$_3$)$_2$
Note:
R = (1–4C)alkyl, such as methyl (Me) or ethyl (Et)
R$^x$ = 1-12C)alkyl
When R$^x$ = H is required, step (i) is omitted and step (iii) becomes:
(a) [(CH$_3$)$_2$CH]$_2$NLi, THF, −78° C.; then (CH$_3$)$_3$SiCl
(b) CH$_2$=CH.—CH$_2$.CH$_2$.CO.O.R, [(CH$_3$)$_2$CH]$_2$NLi, THF, −78° C.
(c) Tetrabutylammonium fluoride, THF

SCHEME 5

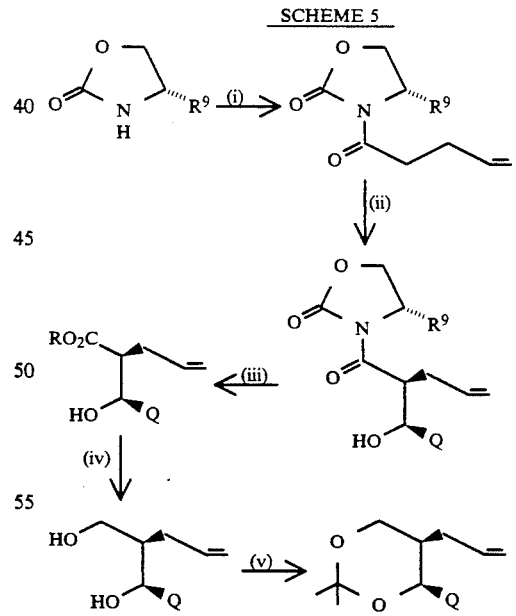

Reagents:
(i) 4-pentenoyl chloride, BuLi, THF, −78° C.
(ii) Bu$_2$B.O.SO$_2$.CF$_3$, [(CH$_3$)$_2$CH]$_2$N.C$_2$H$_5$, Q.CHO, CH$_2$Cl$_2$; then H$_2$O$_2$, pH 7
(iii) NaOR, ROH
(iv) LiAlH, THF
(v) TsOH, Ra.Rb.CO or Ra.Rb.C(OCH$_3$)$_2$
Note:
R = (1–4C)alkyl, such as Me, Et or isopropyl

SCHEME 6

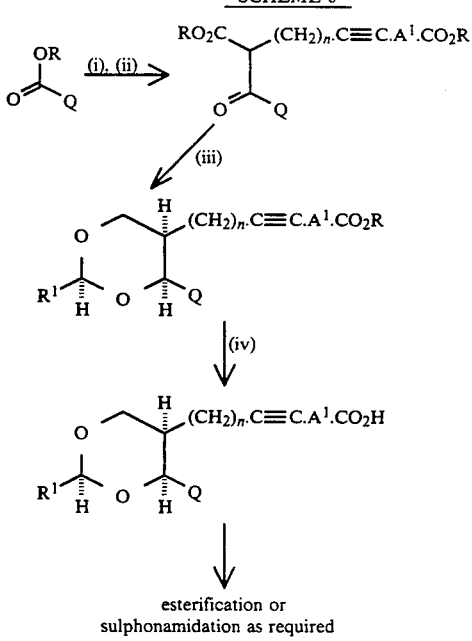

esterification or
sulphonamidation as required

Reagents:
(i) CH$_3$CO$_2$R, NaH
(ii) NaOEt, EtOH, Br(CH$_2$)$_n$.C≡C.A$^1$.CO$_2$R
(iii) NaBH$_4$; then R$^1$CHO, TsOH
(iv) NaOH/ROH Note:
R = (1-4C)alkyl such as Me or Et

What is claimed is:
1. A 1,3-dioxane alkenoic acid derivative of the formula I

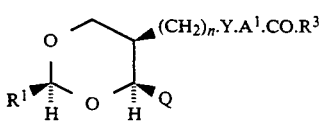

wherein:
n is the integer 1 or 2;
Y is methylenoxy, vinylene or ethylene;
A$^1$ is (1-6C)alkylene;
R$^1$ is a group of the formula R$^2$.A$^2$—, in which:
R$^2$ is phenyl unsubstituted or bearing up to three substituents which are independently selected from (1-6C)alkyl, (1-6C)alkoxy, (2-6C)alkanoyl, (1-6C)alkylthio, (1-6C)alkylsulphonyl, halogeno, trifluoromethyl, nitro and cyano;
A$^2$ is a direct bond to R$^2$ or a group of the formula —W—C(R$^4$)(R$^5$)— wherein W is oxygen, methylene or a direct bond to R$^2$, and R$^4$ and R$^5$ are independently (1-4C)alkyl;
Q is a heterocyclyl group selected from thiazol-5-yl and imidazol-5-yl, the latter being unsubstituted or bearing a (1-12C)alkyl group at the 1-position of the imidazole ring; and
R$^3$ is hydroxy, a physiologically acceptable alcohol residue, or (1-4C)alkanesulphonamido;
or a pharmaceutically acceptable salt thereof.

2. A compound as claimed in claim 1, in which n is 1, Y is cis-vinylene, A$^1$ is ethylene and R$^3$ is hydroxy.

3. A compound as claimed in claim 1 or claim 2, in which A$^2$ is a direct bond to R$^2$ or 1-oxy-1-methylethyl.

4. A compound as claimed in claim 1 or claim 2, in which R$^2$ is 4-methyl-2-nitrophenyl, 4-cyanophenyl, 4-chloro-2-cyanophenyl, 2-cyano-4-ethylphenyl, 4-(1-methylethyl)-2-cyanophenyl, 4-acetyl-2-nitrophenyl, 2-trifluoromethylphenyl or 4-methylthio-2-nitrophenyl.

5. A compound as claimed in claim 1 or claim 2, in which Q is thiazol-5-yl, 1-methylimidazol-5-yl or 1-hexylimidazol-5-yl.

6. 4(Z)-6-[(2S,4S,5R)-2-(1-(4-methyl-2-nitrophenoxy)-1-methylethyl-4-(5-thiazolyl)-1,3-dioxan-5-yl]hexanoic acid, or a pharmaceutically acceptable salt thereof.

7. A pharmaceutical composition, which comprises a pharmacologically effective amount of a compound of the formula I, or a pharmaceutically acceptable salt thereof, as claimed in claim 1, together with a pharmaceutically acceptable diluent or carrier.

8. A method of producing a beneficial effect on the thromboxane A2 system by antagonising one or more of the actions of thromboxane A2 and/or inhibiting its synthesis in a warm-blooded animal which requires such treatment, said method comprising administering to said animal an effective amount of a compound of the formula I, or a pharmaceutically acceptable salt thereof, as claimed in claim 1.

* * * * *